(12) United States Patent
Cramer et al.

(10) Patent No.: US 8,431,774 B1
(45) Date of Patent: Apr. 30, 2013

(54) PLANT-BASED EXPRESSION OF AVIAN INTERLEUKIN-12 AND METHODS OF PRODUCING AND USING SAME

(75) Inventors: Carole L. Cramer, Jonesboro, AR (US); Maureen C. Dolan, Jonesboro, AR (US); Giuliana Medrano, Jonesboro, AR (US); David N. Radin, Jonesboro, AR (US)

(73) Assignee: University of Arkansas-Jonesboro, State University, AR (US)

( * ) Notice: Subject to any disclaimer, the term of this patent is extended or adjusted under 35 U.S.C. 154(b) by 447 days.

(21) Appl. No.: 12/574,598

(22) Filed: Oct. 6, 2009

Related U.S. Application Data

(60) Provisional application No. 61/102,945, filed on Oct. 6, 2008.

(51) Int. Cl.
*A01H 5/00* (2006.01)
*C07K 14/54* (2006.01)
*C12N 15/24* (2006.01)
*C12N 5/04* (2006.01)

(52) U.S. Cl.
USPC ............ 800/288; 530/351; 800/295; 800/298; 800/278; 536/23.1; 536/23.5

(58) Field of Classification Search .................. None
See application file for complete search history.

(56) References Cited

PUBLICATIONS

Kwon et al. (2003, Biotechnol.Bioeng. 81:870-875).*
Gutierrez-Ortega et al. (2004, Biotechnol.Bioeng. 85:734-740).*
Gutierrez-Ortega et al. (2005, Transgenic Res. 14:877-885).*
Liu et al. (2008, J. Interferon Cytokine Res. 28:381-392.*

* cited by examiner

*Primary Examiner* — Elizabeth C Kemmerer
(74) *Attorney, Agent, or Firm* — Joe D. Calhoun; Rashauna A. Norment

(57) ABSTRACT

The invention is a plant-based production of biologically active avian interleukin-12 protein and functional units for increasing the protective and/or immunological response in an animal, for use as an adjuvant with a vaccine to control avian infectious diseases, and methods of producing and using the same. Specifically, avian interleukin-12 was produced from a plant-based expression system and demonstrated that it stimulates production of immune responses in birds.

11 Claims, 17 Drawing Sheets

PLANT-BASED EXPRESSION OF AVIAN INTERLEUKIN-12 AND METHODS OF PRODUCING AND USING SAME

CROSS REFERENCE TO RELATED APPLICATIONS

This application claims a priority date to Provisional Application No. 61/102,945, filed Oct. 6, 2008, the contents of which and all references cited therein are incorporated herein by reference in their entirety.

FEDERALLY SPONSORED RESEARCH AND DEVELOPMENT

This application contains a subject invention made, in part, with Government support under Award No. 2007-33610-17978 (Phase I) Award No. 2008-33610-19482 (Phase II) awarded to BioStrategies LC by the U.S. Department of Agriculture, Cooperative State Research, Education and Extension Service (USDA-CSREES) and Small Business Innovation Research (SBIR).

MICROFICHE APPENDIX

Not applicable.

SEQUENCE LISTING

The accompanying sequence listing is to be incorporated by reference into the application. The content of the sequence listing information recorded in the computer readable form is identical to the written (on paper or compact disc) sequence listing, and, where applicable, includes no new matter, as required by 37 CFR 1.821(e), 1.821(f), 1.821(g), 1.825(b), or 1.825(d). The name of the ASCII text file is 2012-08-17SubstituteSequenceListingProject_ST25.txt; the creation date of the text file is Aug. 17, 2012; and the size of the text file is 9.70 KB.

BACKGROUND OF THE INVENTION

Field of Invention

The present invention generally relates to plant-based production of bioactive avian interleukin-12 (IL-12) protein and fragments for increasing the immune response in animals, and methods of production and use of same.

Domestic and wild fowl, as a major disease reservoir for avian influenza virus, play a central role in the re-emergence of this potentially pandemic disease pathogen. Recent outbreaks of highly pathogenic strains of avian influenza (HPAI) in Asia and Europe have highlighted vulnerabilities of the U.S. poultry industry and the potential for emergence of human transmissible avian influenza pandemic strains. Although high standards of poultry production practices in the U.S. make the industry less susceptible to the rapid spread seen in less developed countries (e.g., through open markets or contact with wild bird populations), the potential impact to the industry and to U.S. exports of poultry could be devastating. The increasing threat of pandemic flu and other infectious diseases to domestic fowl, human populations, as well as endangering our global food supply has prompted governments, commercial organizations, agricultural and medical health agencies in the U.S. and around the world to initiate multifaceted research and development efforts aimed at mitigating this threat. Although much of this effort targets human vaccines and antiviral therapeutics, new technologies for producing inexpensive high-quality veterinary vaccines to control avian flu at its source will be critical for successful intervention in the global disease cycle supporting the threat of pandemic flu and other infectious diseases in both domestic poultry and humans. In order to effectively target this disease threat to domestic poultry, new innovative strategies to produce critical avian disease research reagents and rapidly scalable vaccine components for poultry, such as avian IL-12, are required. While bird vaccines based on killed or attenuated virus have been widely used, these vaccines often vary in quality. A major consequence of "bad vaccines" is that while symptoms may be masked, active virus is shed at levels that support disease spread and viral genome re-assortment. The fear is that partially effective poor vaccines will allow virus-infected carrier birds to transmit the disease while appearing to be protected by these vaccine products. Thus, there is a clear need to develop new commercially available agricultural and veterinary vaccine products including new adjuvants that will be more effective at providing confidence that our poultry industry is secure against any significant disease threat.

Interleukin-12 is a key modulator of cell-mediated immunity and a potent adjuvant, which greatly enhances the efficacy of influenza vaccines in animal studies. Avian Interleukin-12 (IL-12) has not been previously expressed in plants or any other expression system at levels high enough to be useful for any commercial applications. There are currently no commercial sources for IL-12 from any avian species. Furthermore, the plant-based expression levels of IL-12 from diverse animal species are highly variable making it impossible to predict the potential for expression of avian IL-12 in plants.

In addition to needs generated in the vaccine market there are two additional secondary markets where cost effective IL-12 cytokine production could find uses. There are currently no commercial suppliers of avian IL-12 to the research and development reagent market, and other research scientists in animal health have voiced their interest in the prospective availability of this product for research on a variety vaccine development problems. A third prospective area of need is the potential that cytokines (and IL-12 in particular) may find use in feed supplements to promote growth and protection from disease by enhancing the immune system. There is a strong need for alternatives to antibiotic supplements in feed as these are phased out and cytokines could replace these to promote similar benefits.

Interleukin-12 is a complex heterodimeric cytokine molecule composed of an alpha chain (p35) and beta chain (p40) linked by a disulfide bridge. In previous research intranasal delivery of IL-12 with influenza subunit vaccines resulted in significant increases in both mucosal and systemic antibodies that were protective in a lethal influenza virus infection (Arulanandam et al., 1999). Recent studies using aerosol co-administration of IL-12 as a component of a DNA-based influenza vaccine significantly increased neutralizing antibody responses and protected against flu virus challenge in mice (Orson et al., 2006). Recognizing that the main entry route for the transmission of the many pathogenic avian viral disease agents is through mucosal surfaces, the ability to mount a more effective mucosal response to ensure protection is paramount. Intranasal delivery of IL-12 in a vaccine admix enhanced antigen-directed mucosal immunity (secretory IgAs) in a variety of disease models (i.e. Albu et al., 2003; Lynch et al., 2003; Arulanandam et al., 2001a; 2001b; 1999; Huber et al., 2001; Boyaka et al., 1999). These studies and others support IL-12's ability to direct immunity against many viral pathogens. However, the role of IL-12 in a vaccine is complex and greatly influenced by route of delivery, vaccine formulation, dosage, and vaccine schedule (e.g. Sacco et al., 1997). In addition, the protein itself is large (approximately 70 kDa) and complex presenting challenges for large scale bio-production of recombinant bioactive IL-12 protein required for many potential clinical applications. Previous attempts to produce human IL-12 in plants (Kwon et al, 2003; Gutierrez-Ortega 2004, 2005) yielded IL-12 at very low levels and demonstrated only partial IL-12 activity. In contrast, mouse IL-12, appears to be very effectively produced at high levels in plants (Liu et al., 2008. J. Interferon Cytokine Res. 28: 381-392). As shown in FIG. 1, almost 1000-fold differences in product yields have been observed in direct comparisons of human IL-12 (hIL-12) and murine IL-12 (mIL-12) sequences expressed in both transient expression systems and in stable transgenic plants and using vector constructs that vary only in the human versus mouse sequence. In the transient expression system used in this invention, comparable mRNA transcript levels were detected suggesting that the difference lies at the translational or post-translational levels. The fact that these closely related mammalian homologs show such radically different expression levels in plants is particularly surprising since mIL-12 is structurally so similar to human IL-12 that it interacts with human IL-12 receptors to trigger immune activation. These results support the conclusion that the ability of plants to produce useful levels of bioactive IL-12 from different animal species cannot be predicted based either on sequence similarities or on previous success in IL-12 genes from other species.

Sequences encoding avian IL-12 (both p35 and p40 subunits) have only recently been identified (Degen et al., 2004) and the ability of this IL-12 homolog to enhance protection of birds against avian disease virus has not been tested due to lack of available reagents. IL-12 is a potent adjuvant and key modulator of cell-mediated immunity, which has been shown to greatly enhance the efficacy of avian disease vaccines in animal studies. The inventors have developed a plant-based bio-production system for the avian IL-12 protein that produces very high commercial scale levels of recombinant protein with signature immune-modulating bioactivity. Although the inventors previously produced high commercial scale yields of mouse IL-12 in plants, they found that yields of the very closely related human were very low thus demonstrating the low predictive value of successful plant-based IL-12 protein expression from one species to another.

U.S. Pat. No. 7,347,996 B1 issued to Degen et. al discloses avian equivalents of the mammalian p40 based cytokines. It further discloses sequences, p40 and p35, derived from chicken DNA, and that avian IL-12 may be used as an adjuvant in avian vaccines to enhance the immune response. It also discloses that proteins may comprise only a functional fragment of the p40 or p35 subunit (or both). It notes that avian IL-12 can be generated via expression vectors containing both the p35 and p40 cDNAs separated by an element to form a single open reading frame. It further disclosed that the bioactivity of proteins can be measured in vitro using a proliferation assay. It discloses that an adjuvant composition according to Degen comprises a protein per the invention, preferably avian IL-12, and a pharmaceutically acceptable carrier.

U.S. Pat. No. 5,891,680 issued to Lieschke et al. discloses DNA encoding a bioactive IL-12 protein, wherein the bioactive IL-12 protein comprises a native IL-12 p35 subunit and native IL-12 p40 subunit joined by a polypeptide linker. It further discloses a method of producing a bioactive IL-12 protein comprising the steps of (a) providing an expression vector comprising DNA encoding native IL-12 p35 subunit, DNA encoding a polypeptide linker and DNA encoding native IL-12 p40 subunit; (b) introducing the expression vector into an appropriate host cell; and maintaining the host cell resulting from step (b) under conditions appropriate for expression of the DNA present in the expression vector. It further discloses that the native IL-12 p35 subunit and the native IL-12 p40 subunit are of human or mouse origin.

Published U.S. patent application Ser. No. 10/243,075 (Publication No. US20030129161) submitted by Chu et al., discloses a composition for enhancing the immunogenicity of a veterinary vaccine that comprises a pharmacologically effective amount of IL-12 serving as an immunomodulator. The combination comprising an immunomodulator in conjunction with immunoadjuvants enhances the immunogenicity or physiological efficacy of veterinary vaccines containing an antigen. It also discloses the use of IL-12 for enhancing or accelerating the immunogenicity of weak, immunosuppressive or marginally safe antigens.

None of the patents cited disclose a plant-produced biologically active avian IL-12 or a plant-produced biologically active chicken IL-12 having an increased protective and/or immunological response to avian influenza in an animal.

BRIEF SUMMARY OF THE INVENTION

The general focus of this invention was to develop new high valued health related agricultural products through the application of biotechnological research approaches. This project focused on the bio-production of avian IL-12 and methods for producing and using the same to address needs involving (i) producing inexpensive high-quality veterinary vaccines to control avian diseases; and (ii) producing avian immunological and vaccine research reagents and rapidly scalable vaccine components for poultry. The invention discloses a plant expressing a biologically active avian IL-12 protein or biologically active fragment thereof. This includes the cell of the plant. The method for producing comprises the steps of transforming a plant cell with a nucleic acid sequence that encodes an IL-12 protein, cultivating a transformed plant host under conditions to express IL-12 protein, and recovering the expressed biologically active avian IL-12 protein or fragment thereof from the plant cell. The avian IL-12 protein or fragment thereof is transiently expressed in the plant cell. Alternatively, the avian IL-12 protein or fragment thereof is stably expressed in the plant cell. The avian IL-12 protein is produced by expressing in the plant cell at least one p35 alpha chain and at least one p40 beta chain such that at least one p35 alpha chain and at least one p40 beta chain form the protein in the plant cell. The composition comprises a biologically active avian interleukin-12 protein produced in pharmacologically desirable amounts by a plant-based expression system. The biologically active avian interleukin-12 protein comprises chicken IL-12 produced at levels of at least about 0.1% total soluble protein. A component of a plant is selected from the group consisting essentially of seed, leaf, root, stem and tissue of the plant, and combinations and mixtures thereof.

The method for administering a composition to birds comprising a biologically active avian IL-12 protein or fragment thereof occurs by expressing the protein or fragment thereof in a plant cell, and administering a composition comprising the protein or fragment thereof to the bird. The composition is administered such that it protects the bird from disease. The IL-12 protein or fragment thereof is administered by a method selected from the group consisting essentially of mucosal, oral and intravenous administration, and combinations and mixtures thereof. The avian IL-12 protein or fragment thereof is extracted from the plant cell prior to administration to the animal. The plant cell comprising the avian IL-12 protein or fragment thereof is then administered to the bird. The avian IL-12 protein or fragment thereof is administered to the bird such that the protein or fragment thereof produces an immune response in the bird. Moreover, the avian IL-12 protein or fragment thereof is administered to the bird such that the protein or fragment thereof elicits production of interferon-gamma in the bird.

This project successfully demonstrated the feasibility of plant-based production of bioactive avian IL-12. Also described are means and methods to exploit and develop this product as an effective adjuvant for enhancing the efficiency and effectiveness of vaccines against avian influenza and other poultry diseases. The inventors isolated and tested multiple avian IL-12 gene constructs and demonstrated significant expression levels in plants. They selected a His-tagged native avian IL-12 gene construct that provides product yields sufficient to support scaled up production and purification of avian IL-12 protein for commercial applications in the research and development reagent market. Most importantly, they demonstrated that plant-synthesized avian IL-12 shows excellent immune stimulating bioactivity in signature in vitro bioassays using chicken or turkey splenocytes, a standard cellular test for immune stimulation activity. Poultry in vivo trials confirmed that plant-produced avian IL-12 stimulates production of antibodies against model viral antigens. These results showed that plant-produced avian IL-12 has significant potential to function as a vaccine adjuvant in vaccines for avian influenza and other infectious veterinary diseases.

One primary object of the present invention is to provide a plant-produced bioactive avian IL-12 protein and functional units that direct an increased protective and/or immunological response in an animal.

Another primary object of the present invention is to provide a composition comprising a veterinary vaccine to control diseases in domestic fowl, and methods for producing and administering the same.

Another primary object of the present invention is to provide a composition comprising avian immunological research reagents and vaccine components for poultry and method for producing and administering the same.

Another primary object of the present invention is to provide a composition comprising avian health-promoting immune-stimulant for poultry and method for producing and administering the same.

Another object of the invention is to provide a composition, and method of producing avian IL-12 in plants at levels high enough to be useful in commercial applications.

Other objects will be apparent from a reading of the written description disclosed herein, together with the claims.

DETAILED DESCRIPTION OF THE INVENTION

Figure 1:
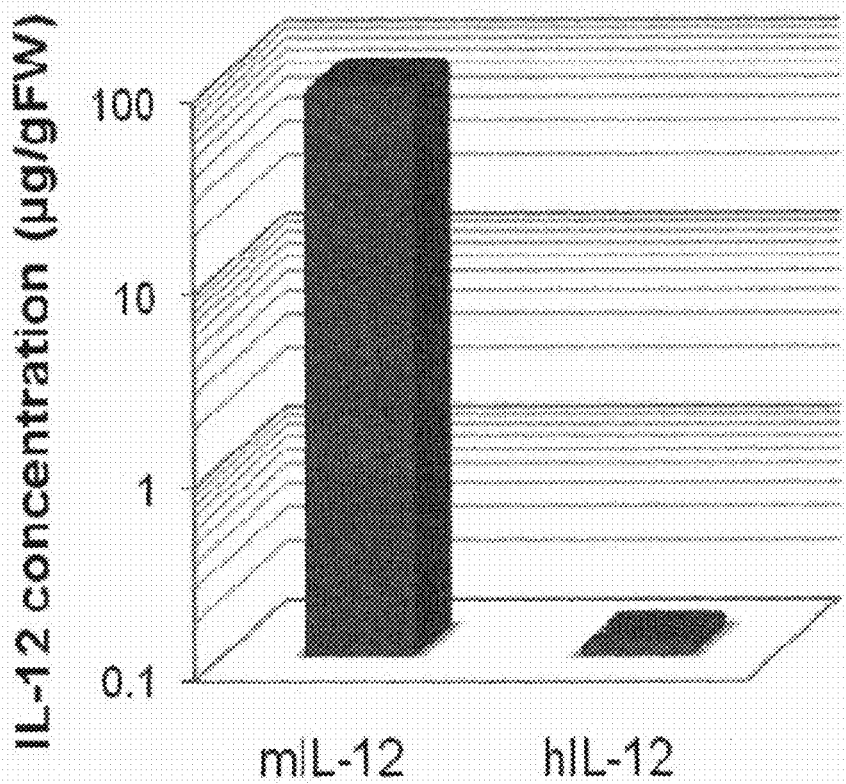
FIG. 1 is a comparison of IL-12 production levels in leaves of *Nicotiana benthamiana* transiently expressing either sequences encoding a single-chain form (p40-linker-p35) of murine IL-12 (mIL-12) or human IL-12 (hIL-12). [Note: logarithmic scale].

For the sake of simplicity and to give the claims of this patent application the broadest interpretation and construction possible, the following definitions will apply:

The term "avian animal" or "avian" essentially means all avian species, whether domesticated or wild.

The term "avian IL-12 protein" essentially means avian interleukin-12 protein and/or functional units.

The term "product" essentially means plant-produced bioactive avian interleukin-12 protein and/or fragments whether they are purified or not. The term "product" also encompasses plants, plant parts, and plant cells containing expressed avian IL-12

The term "His-tag" or "histidine-tag" essentially means a polyhistidine domain of 4 to 10 histidines incorporated into the protein product to aid in detection and purification.

The terms "interleukin-12" (IL-12) or IL-12 "fragments" are meant to include related sequences capable of triggering IL-12 mediated responses in avian species and/or in avian immune responsive cells. Avian Interleukin-12 (IL-12) is a complex heterodimeric cytokine molecule composed of an alpha chain (p35) and beta chain (p40) linked by a disulfide bridge. References to "fragments" includes either of these subunits singly or in combination and any part of these sequences exhibiting biological activity.

References to a "biologically active" avian IL-12 protein or "biologically active" fragment or functional variant thereof is intended to refer to an IL-12 that is capable of producing a protective or immune response when administered to an animal or which will enhance a protective or immune response in an animal. A functional fragment and a biologically active fragment may be polypeptides that are functional per se, or functional when linked to other polypeptides. The subunits of the alpha chain (p35) and beta chain (p40) are examples of such biologically active fragments. A functional fragment of the polypeptide is a fragment that at least represents the part(s) of the polypeptide sub-unit(s), which is/are essential for the protein to be able to serve as a cytokine, and can fulfill this function, for example, when used alone or fused to heterologous sequences. The term "biologically active" further essentially means stimulating a protective response and an immunological response that involves without limitation promoting a long-term and stable T-helper-cell type-1 (Th-1)-driven immune response, increasing Th1 cytokines and particularly interferon gamma (IFN-γ) production and blocking the differentiation of Th2 cells; serving as a potent growth factor in activating T-cells and natural killer (NK) cell proliferation and enhancing cytolytic T-cell and NK cell cytotoxicity; promoting a powerful antitumor and antimetastatic activity; functioning as an immunostimulatory nutritional/food additive and combinations and mixtures thereof. In addition biologically active can mean significant reduction in the severity of an infection by a pathogen. Biological activity typically involves the heterodimeric IL-12 p70 but also individual subunit components such as p40 and/or oligomers of said subunits such as p80 (dimeric p40) that can be antagonistic to above mentioned IL-12 activity.

The term "immune response" essentially means a response to an antigen or antigenic determinant by the immune system of an animal. Exemplary immune responses include, without limitation, cytokine production, humoral immune responses, such a production of antigen-specific antibodies; cell-mediated immune response (such as T-cell and B-cell response); mucosal immune response (such as IgA production); systemic immune response such as a response lymph node-spleen- or gut-associated lympoid tissues. It can include, for example and without limitation, a cellular or humoral response. The term "immunological response" further means immunogenic responses that include, without limitation, functioning as a promising vaccine adjuvant, enhancing the primary Th1 response when given in conjunction with other adjuvants, improving overall immune function, and/or preventing IgE-mediated allergic conditions. The term "immune response" also means a response to an antigen or antigenic determinant by the immune system of an animal. Exemplary immune responses (without intending to be limiting) include cytokine production, humoral immune responses, such a production of antigen-specific antibodies; cell-mediated immune response (such as T-cell and B-cell response); mucosal immune response (such as IgA production); systemic immune response such as a response lymph node-spleen- or gut-associated lympoid tissues. It can include, for example and without limitation, a cellular or humoral response. To induce such immunological response, IL-12 can be administered to birds as part of a vaccine formulation either before or after hatching using methods known in the art.

The terms "protecting" or "protection" as used herein, are intended to mean that the host animal may or may not produce an immunogenic response that can be measured, yet the degree or severity of symptoms are reduced and morbidity and mortality reduced after the animal is exposed to a disease, as compared to an animal that has not received the IL-12 protein or fragment thereof of the invention. Furthermore, protection also includes a lessening in severity of any gross or histopathological changes and/or of symptoms of the disease, as compared to those changes or symptoms typically caused in animals that are unprotected (i.e., relative to an appropriate control. Thus there may be a measurable immune response, or there may not, and the IL-12 protein or fragment thereof might, for example, but used as an adjuvant. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

References to "stable expression" mean the expression of a protein or fragment thereof such that the gene or DNA sequence coding for the protein or fragment is incorporated into the genome of the plant or plant cell.

The term "transient expression" is short term activity of a transgene coding for an expressed protein following introduction of its transgene into a plant cell but not integrated stably into the plant genome. Introduction of the transgene can be by means of *Agrobacterium*-mediated methods, viral-mediated methods, mechanical methods or combinations thereof.

The term "recovery" refers to isolation of the expressed protein or polypeptide fragment wherein the protein or fragment is extracted from the plant, and may or may not be subject to further purification. The expressed protein or fragment may also be "recovered" in the form of a seed or other plant tissue or organ containing the expressed protein or fragment.

The term "animals," essentially includes, but is not limited to, mammals and birds. The exemplary term "mammals" include, but are not limited to, mice, rats, guinea pigs, rabbits, ferrets, dogs, cats, cows, horses and primates including man. The term "avian" essentially means all avian species, whether domesticated or wild.

Also for the sake of simplicity and to give the claims of this patent application the broadest interpretation and construction possible, the conjunctive "and" may also be taken to include the disjunctive "or," and vice versa, whenever necessary to give the claims of this patent application the broadest interpretation and construction possible. Likewise, when the plural form is used, it may be taken to include the singular form, and vice versa.

Described here are compositions of matter and methods of producing and using plant-produced avian IL-12 proteins and fragments thereof. For the first time, plant production of bioactive avian IL-12 is described. Experimentation was successful in developing ChIL-12 gene constructs, characterizing ChIL-12 produced in leaf material, and demonstrating the immunomodulating bioactivity of plant-produced ChIL-12. Further described are ChIL-12 adjuvant production scale-up, efficacy in poultry vaccine trials, assessment of ChIL-12 activity across avian species, and tests to address efficacy with oral delivery. Co-formulation of this strong immune stimulating adjuvant with avian vaccines may ensure that these poultry vaccines elicit sufficient immunity to prevent avian flu transmission at the avian source. Plant-based bio-production can provide the cost and scale advantages to enable these benefits to be widely integrated into avian vaccine strategies for both domestic and wild bird populations.

One embodiment of the invention is a composition and method for producing avian IL-12 protein or a fragment thereof expressed in a plant cell. In another embodiment, the plant-produced avian IL-12 protein or fragments thereof has IL-12 activity. In another embodiment is a composition and method for producing avian IL-12 protein or fragment thereof that is expressed at high levels in a plant cell. In yet another embodiment, avian IL-12 protein or fragments thereof is expressed in a plant cell, such that it expresses at levels of at least 0.1% total soluble protein. In another embodiment, avian IL-12 protein or fragments thereof is expressed at levels of at least about 1% total soluble protein. A further embodiment provides the plant cell is from a multiple species of plants. An embodiment provides the plant cell is a tobacco or flax plant cell.

Avian IL-12 is a heterodimeric molecule composed of an alpha chain (p35) and beta chain (p40) linked by a disulfide bridge or amino acid linker to form the biologically active heterodimer. When referring to avian IL-12, it is intended to include the avian interleukin-12 protein and its fragments. Avian IL-12 refers to interleukin-12 and related sequences that are capable of triggering IL-12-mediated responses in avian species and/or in avian immune responsive cells. In a preferred embodiment, the bioactive IL-12 product is produced by expressing a single-chain form comprising the p40 subunit, a flexible amino acid linker- and the p35 subunit. In another preferred embodiment, the alpha and beta chains are expressed from separate gene sequences.

Also encompassed within the invention is the production in plants of fragments of avian IL-12. These fragments are preferably those which will induce a protective and/or immunogenic response in an animal or will enhance a protective and/or immunogenic response. A protective response does not necessarily produce immune cells in an animal, but reduces morbidity or mortality to the disease. Proteins comprising only a functional fragment of the p40 or p35 sub-unit (or both) are likewise considered as part of the present invention. A functional fragment of the polypeptide is a fragment that at least represents the part(s) of the polypeptide sub-unit(s), which is/are essential for the protein to be able to serve as a cytokine, and can fulfill this function, for example, when used alone or fused to heterologous sequences. Thus, such functional fragments may be polypeptides that are functional per se, or may be functional when linked to other polypeptides, to obtain chimeric proteins. These functional fragments are understood to fall within the definition of the subunits.

The invention is further to "functional variants" of the IL-12 protein and its functional fragments and subunits. Functional variants include, for example, IL-12 polypeptide sequences having one or more amino acid substitutions (or substitutions in the nucleotide sequence encoding same), deletions or insertions and wherein the variant retains biological activity, particularly the ability to producing a protective or immune response when administered to an animal or which will enhance a protective or immune response in an animal. A functional variant is a biologically active variant that may be polypeptides that are functional per se, or functional when linked to other polypeptides. Variants of the subunits of the alpha chain (p35) and beta chain (p40) are examples of such biologically active variants. Likewise, avian IL-12 and functional variants thereof may be polypeptides that have been modified to include an epitope-tag, a purification-tag, a His-tag or other alterations that may provide benefit but do not impair the IL-12 bioactivity. Functional variants can be created by any of a number of methods available to one skilled in the art, such as by site-directed mutagenesis, induced mutation, identification as allelic variants, cleaving through use of restriction enzymes, genetic fusions, or the like. Activity can likewise be measured by any variety of techniques, including measurement of production of ChIFN-γ or similar techniques or measurement of cytokine activity, described infra.

Plant-produced avian IL-12 can also be used as an adjuvant with a vaccine to increase the beneficial impact of the vaccine and/or to reduce transmission of the disease to other animals. In one embodiment, avian IL-12 is used in conjunction with an immunogen for which it is desired to elicit an immune response. For example, in avian vaccines such as those against Marek's disease, Newcastle Disease Virus, and other pathogens including Infectious Bursal Disease Virus, Infectious Bronchitis Virus, and Fowlpox Virus, it is desirable to include avian IL-12 in the vaccine to enhance the magnitude and quality of the immune response. Likewise, it is desirable to include avian IL-12 in vaccines to enhance protection against parasitic diseases such as Coccidiosis. The foregoing are examples of diseases for which the cytokine may be used, and are not intended to be limiting.

Any method of exposing the animal to the plant-produced avian IL-12 may be used, and the invention is not limited by the mode of contacting the animal with the protein or fragment, whether feeding the plant tissue comprising the protein or fragment, or any of many known methods, such as parenterally or intramuscularly by injection, rapid infusion, nasopharyngeal absorption, dermal absorption, and bucal or oral absorption. In one embodiment, a feed product comprising the IL-12 containing plant cells or tissues or organs may be fed to the animal. As discussed further below, the protein or fragments thereof may also be extracted from the plant and administered to animals.

IL-12 may be administered in conjunction with a live (i.e., replicating) vaccine or a non-replicating vaccine. Non-limiting examples of replicating vaccines are those comprising native or recombinant viruses or bacteria, such as modified turkey herpes virus or modified fowl pox virus. Non-limiting examples of non-replicating vaccines are those comprising killed or inactivated viruses or other microorganisms, or crude or purified antigens derived from native, recombinant, or synthetic sources, such as Coccidial vaccines. Commercial sources for avian vaccines include without limitation: Rhone Merieux Laboratoire-IFFA (Lyon, France); Intervet International BV (Boxmeer, The Netherlands); Mallinckrodt Veterinary; Solvay Animal Health (Mendota Heights, Minn.); Hoechst-Roussel (Knoxyille, Tenn.); and Nippon Zeon Co., Ltd. (Kawasaki-Kiu, Japan).

One embodiment provides a method in which plant-produced avian IL-12 protein or fragment thereof is administered to an animal to provide increased protection from and/or immune response to disease. In another embodiment of the invention, a method is provided in which plant-produced avian IL-12 protein or fragment thereof is added as an adjuvant with a vaccine to increase protection from and/or immune response to a disease. In another embodiment, immunogenicity provided by a vaccine is increased by combining plant-produced avian IL-12 protein or fragment thereof with the vaccine. In one embodiment, the animal is an avian animal selected from the group consisting of but not limited to chicken, turkey, geese and duck. In another embodiment the plant-produced avian IL-12 protein or fragment thereof is administered to the avian animal or an avian animal egg by injection. An embodiment provides the plant-produced avian IL-12 protein or fragment thereof is administered to the avian animal orally. An embodiment provides that the plant-produced avian IL-12 protein or fragment thereof is mucosally administered to the animal. Mucosal administration includes nasal, inhalational, reproductive and anal routes of administration. In another embodiment, the plant-produced avian IL-12 protein or fragment thereof is administered using the intact plant cells prior to extraction. In a further embodiment, the plant-produced avian IL-12 protein or fragment thereof is administered using intact plant cells, which include plant seeds and tissues. In another embodiment, the plant-produced avian IL-12 is used such that the extracted or unextracted IL-12 is used as an animal feed supplement.

In another embodiment, plant-produced avian IL-12 is used for enhancing the growth of avian species for medical and/or commercial purposes by promoting immune health. The required amount of IL-12 can be determined by routine experimentation well-known in the art, such as by establishing a matrix of dosages and frequencies and comparing a group of experimental units or subjects to each point in the matrix.

In yet another embodiment, the plant-produced avian IL-12 protein or fragments thereof is used in a manner such that the IL-12 is used as a research reagent.

Expression of the avian IL-12 in plant cells may be accomplished by preparing a construct comprising a nucleic acid molecule encoding the same. Clearly, one skilled in the art appreciates that such constructs can take many different forms and yet achieves the goal of expressing the avian IL-12 either with or without the molecule of interest and any other desired components. Constructs may encode the IL-12 components as a single-chain form that includes coding regions for the p40 subunit, a linker, and the p35 subunit wherein the p40 subunit includes a signal peptide and the p35 subunit represents the mature p35. Alternatively, constructs may encode each IL-12 subunit separately as a distinct gene, which can be carried on the same vector or on separate vectors. A promoter may be used to drive expression of one or more of the above. A selection marker may optionally be included. In other embodiments, the expression construct can contain two or more nucleotide sequences encoding avian IL-12, which could be linked to the same promoter or different promoters. What is more, as discussed below, viral replication in plants may employ entirely different delivery methods. The precise methodology used will vary depending upon the goal to be achieved.

Promoter elements can be those that are constitutive or sufficient to render promoter-dependent gene expression controllable as being cell-type specific, tissue-specific or time or developmental stage specific, or being inducible by external signals or agents. Promoter elements employed to control expression of product proteins and the selection gene can be any host-compatible promoters. When used with plant host cells, these can be plant gene promoters, such as, for example, the ubiquitin promoter (European patent application no. 0 342 926); the promoter for the small subunit of ribulose-1,5-bisphosphate carboxylase (ssRUBISCO) (Coruzzi et al., (1984) *EMBO J.* 3, 1671-1679 and Broglie et al. (1984) *Science* 224, 838-843; or promoters from the tumor-inducing plasmids from *Agrobacterium tumefaciens*, such as the nopaline synthase, octopine synthase and mannopine synthase promoters (Velten and Schell, (1985) *Nucleic Acids Res.* 13, 6981-6998) that have plant activity; or viral promoters such as the cauliflower mosaic virus (CaMV) 19S and 35S promoters (Guilley et al., (1982) *Cell* 30, 763-773; Odell et al., (1985) *Nature* 313, 810-812), the figwort mosaic virus FLt promoter (Maiti et al., 1997) *Transgenic Res.* 6, 143-156; or the coat protein promoter of TMV (Grdzelishvili et al., (2000) *Virology* 275, 177-192.

The range of available host compatible promoters includes tissue specific and inducible promoters. An inducible regulatory element is one that is capable of directly or indirectly activating transcription of one or more DNA sequences or genes in response to an inducer. In the absence of an inducer, the DNA sequences or genes will not be transcribed. Typically the protein factor that binds specifically to an inducible regulatory element to activate transcription is present in an inactive form, which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A host cell containing an inducible regulatory element may be exposed to an inducer by externally applying the inducer to the cell or plant such as by spraying, watering, heating or similar methods.

Any inducible promoter capable of driving expression in a host plant can be used in the instant invention. See Ward et al. (1993) *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. (1993) *PNAS* 90: 4567-4571 (1993)); In2-1 and In2-2 gene which respond to benzenesulfonamide herbicide safeners (U.S. Pat. No. 5,364,780; the GST promoter, which is activated by hydrophobic electrophilic compounds that are used as pre-emergent herbicides; and the PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425; and McNellis et al. (1998) *Plant J.* 14(2):247-257); and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

The expression cassette may also include at the 3' terminus of the isolated nucleotide sequence of interest, a transcriptional and translational termination region functional in the host. The termination region can be native with the promoter nucleotide sequence of the present invention, can be native with the DNA sequence of interest, or can be derived from another source. Thus, any convenient termination regions can be used in conjunction with the promoter of the invention, and are available from the Ti-plasmid of *A. tumefaciens*, such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Natl. Acad. Sci. USA* 86:6126-6130; potyvirus leaders, for example, TEV leader (Tobacco Etch Virus), Allison et al. (1986); *MDMV leader* (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV), Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, vacuole, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like. As noted herein, in particular applications of the invention an endoplasmic reticulum targeting sequence is provided preferentially directing expression to the endoplasmic reticulum of the cell. Signal peptides are also employed in embodiments of the invention, and are useful particularly when expressing avian IL-12 in the host cell and achieving proper folding of the avian IL-12 protein. Targeting may also be used in delivery of the avian IL-12 and the molecule of interest in the target cell. Any functional signal peptide will function for this purpose. For various reasons, targeting to other cellular components may also be desired. A variety of such sequences are known to those skilled in the art. For example, if it is preferred that expression be directed to the cell wall, this may be accomplished by use of a signal sequence and one such sequence is the barley alpha amylase signal sequence, (Rogers, (1985) *J. Biol Chem* 260, 3731-3738). Another example is the brazil nut protein signal sequence when used in canola or other dicotyledons. Directing expression with nuclear localization signals may also be useful. Such nuclear localization signals are know, such as Pro-Lys-Lys-Lys-Arg-Lys-Val which can act as a nuclear location signal. Kalderon et al. (1984) "A short amino acid sequence able to specify nuclear location" *Cell* 39 (3 Pt 2): 499-509. Expressing the protein in the endoplasmic reticulum of the host cell is accomplished through various sequences available. This may be accomplished by use of a localization sequence, such as KDEL. This sequence contains the binding site for a receptor in the endoplasmic reticulum. Munro, S, and Pelham, H. R. B. (1987) *Cell* 48:899-907. The patatin signal sequence is also frequently employed in cell expression. Iturriaga et al. (1989) *The Plant Cell*, Vol. 1, 381-390.

In preparing the expression cassette, the various nucleic acid fragments can be manipulated, so as to provide for the sequences in the proper orientation and, as appropriate, in the proper reading frame. Toward this end, adapters or linkers can be employed to join the fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved. Alternatively, direct synthesis of the gene or components of the gene or expression cassette can be employed.

Reporter genes can be included in the transformation vectors. Examples of suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330. Selectable marker genes for selection of transformed cells or tissues can be included in the construct. These can include genes that confer antibiotic resistance or resistance to herbicides. Examples of suitable selectable marker genes include, but are not limited to: genes encoding resistance to kanamycin including neomycin phosphotransferase, see, e.g., Fraley et al, (1983) *Proc. Natl. Acad. Sci. USA* 80:4803; Miki et al. (1993) "Procedures for Introducing foreign DNA into plants" *Methods in Plant Molecular Biology and Biotechnology*", Glick et al. (eds.) pp. 67-68 (CRC Press 1993); chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Expression of a linked sequence can be tracked by providing useful so-called screenable or scorable markers. The expression of the linked protein can be detected without the necessity of destroying tissue. By way of example without limitation, detectable markers include a β-glucuronidase, or uidA gene (GUS), which encodes an enzyme for which various chromogenic substrates are known (Jefferson, R. A. et al., 1986, *Proc. Natl. Acad. Sci. USA* 83:8447-8451); chloramphenicol acetyl transferase; alkaline phosphatase; a R-locus gene, which encodes a product that regulates the production of anthocyanin pigments (red color) in tissues (Dellaporta et al., in *Chromosome Structure and Function*, Kluwer Academic Publishers, Appels and Gustafson eds., pp. 263-282 (1988); Ludwig et al. (1990) *Science* 247:449); a p-lactamase gene (Sutcliffe, *Proc. Nat'l. Acad. Sci. U.S.A.* 75:3737 (1978)), which encodes an enzyme for which various chromogenic substrates are known (e.g., PADAC, a chromogenic cephalosporin); a xylE gene (Zukowsky et al., *Proc. Nat'l. Acad. Sci. U.S.A.* 80:1101 (1983)), which encodes a catechol dioxygenase that can convert chromogenic catechols; an α-amylase gene (Ikuta et al., *Biotech.* 8:241 (1990)); a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin a green fluorescent protein (GFP) gene (Sheen et al., *Plant J.* 8(5):777-84 (1995)); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); DS-RED EXPRESS (Matz, M. V. et al (1999) *Nature Biotech.* 17:969-973, Bevis B. J. et al. (2002) *Nature Biotech* 20:83-87, Haas, J. et al. (1996) *Curr. Biol.* 6:315-324); *Zoanthus* sp. yellow fluorescent protein (ZsYellow) that has been engineered for brighter fluorescence (Matz et al. (1999) *Nature Biotech.* 17:969-973, available from BD Biosciences Clontech, Palo Alto, Calif., USA, catalog no. K6100-1); and cyan florescent protein (CYP) (Bolte et al. (2004) *J. Cell Science* 117:943-54 and Kato et al. (2002) *Plant Physiol* 129:913-42).

Any plant cell is useful as the host plant cell of the invention, whether monocot or dicot. Examples include corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum; N. benthamiana*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), flax (*Linum usitatissimum*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, vegetables, ornamentals, and conifers. When referring to a plant cell it is also intended to include protoplasts, that is, a cell consisting of the cell membrane and all of the intracellular components, but devoid of a cell wall.

The particular transformation protocol will vary depending upon the host. In plants, suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMKO J.* 3:2717-2722; viral replication systems, Turpen et al, U.S. Pat. Nos. 6,660,500 and 6,462,255; and ballistic particle acceleration, see for example, Sanford et al. U.S. Pat. No. 4,945,050, Tomes et al. (1995) in *Plant Cell, Tissue, and Organ Culture Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Bio/Technology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, New York), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*).

The plant cells that have been transformed may or may not be grown into plants in accordance with conventional methods. See, for example, McCormick et al. (1986) *Plant Cell Reports* 5:81-84. These plants can then be grown and pollinated with the same transformed strain or different strains.

Results described here were obtained, in part, using an transient protein expression system. This system utilized the *Agrobacterium* transfection system for introduction of IL-12 genes into intact *Nicotiana benthamiana* plant tissues and efficient assessment of transgene product yields and quality. The inventors routinely use this method to test the in planta production potential of a new transgene. Based on the presence of polyadenylated transgene mRNA, N-linked glycosylation of transgene product, and assembly of multimeric protein from transgenes delivered from distinct *Agrobacterium* strains, they are confident that the products of the transient system reflect synthesis within the plant cell. They have also exploited this system to compare in planta productivity of constructs that varying codon usage, signal peptides, targeting information, and orientation of fusion partners. For comparative analyses, standardization of promoters/vectors [e.g., they use the double-enhanced 35S promoter (Kay et al., 1987) with TEV enhancer (Carrington et al., 1990) in a pBIB-Kan transformation vector (Becker et al., 1990)], infiltration parameters, control over the developmental stage of experimental plants is key to producing reliable data. Under these conditions, they have observed consistency of product yields (less than 10% variability) using the same construct but significant differences in yields between transgenes or transgene variants. Thus, the inventors believe that products of transient expression effectively reflect any particular plant's intrinsic ability to effectively "read" the transgene and support transcript/protein stability. Because the transient system does not involve chromosomal integration, these differences do not reflect chromosomal "position effects". Based on the inventors' experience, outcomes from transient expression predict relative productivity of transgenic protein in stably transformed plants or hairy roots, although yields are always greater per unit fresh weight or soluble protein in the transient system (Medrano et al, 2009). Other transient expression systems or transfection systems in plants, whether mediated by *Agrobacterium*, viral vectors, or mechanical means, or a combination, are also useful methods for plant-based expression of avian IL-12.

Figure 2:
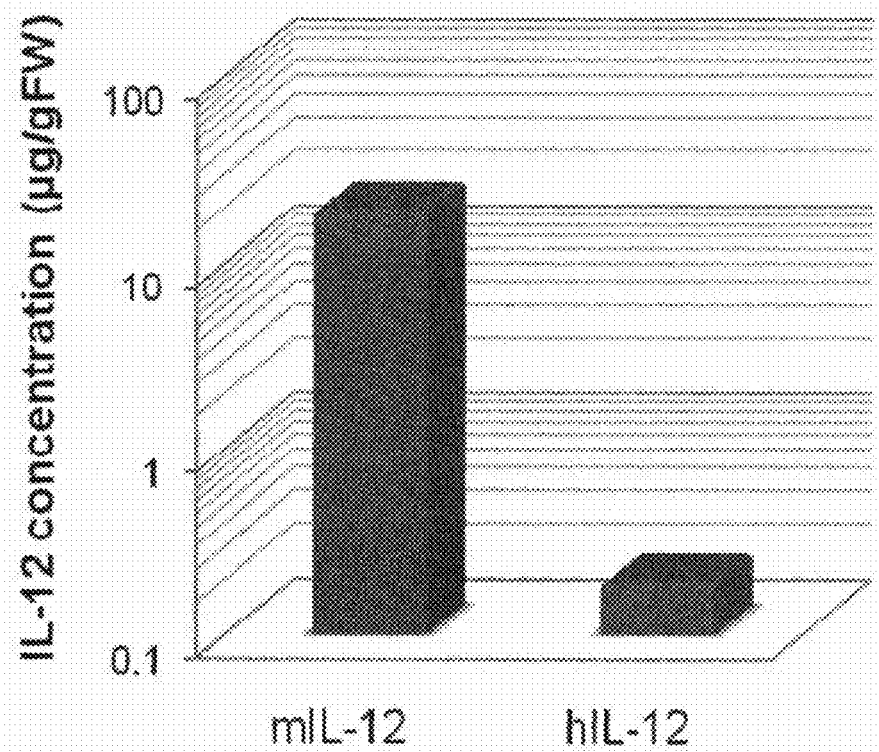
FIG. 2 is a comparison of production levels of mIL-12 or hIL-12 70 kDa heterodimer in leaves of *N. benthamiana* transiently co-expressing vectors encoding the IL-12p35 subunit and the IL-12 p40 subunit. [Note: logarithmic scale].
Figure 3:
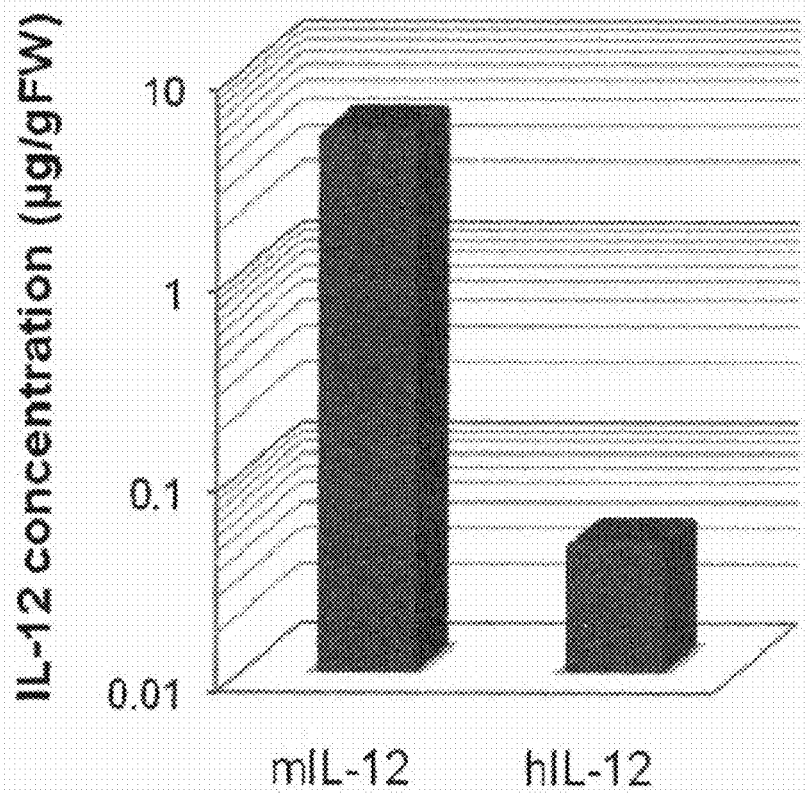
FIG. 3 is a comparison of production levels of IL-12 in leaves of transgenic tobacco (*Nicotiana tabacum*) plants stably transformed with genes encoding the single-chain form of either mIL-12 or hIL-12. Plants represent the highest expressing plant among 30-60 independent transgenic lines. [Note: logarithmic scale].
Figure 4:
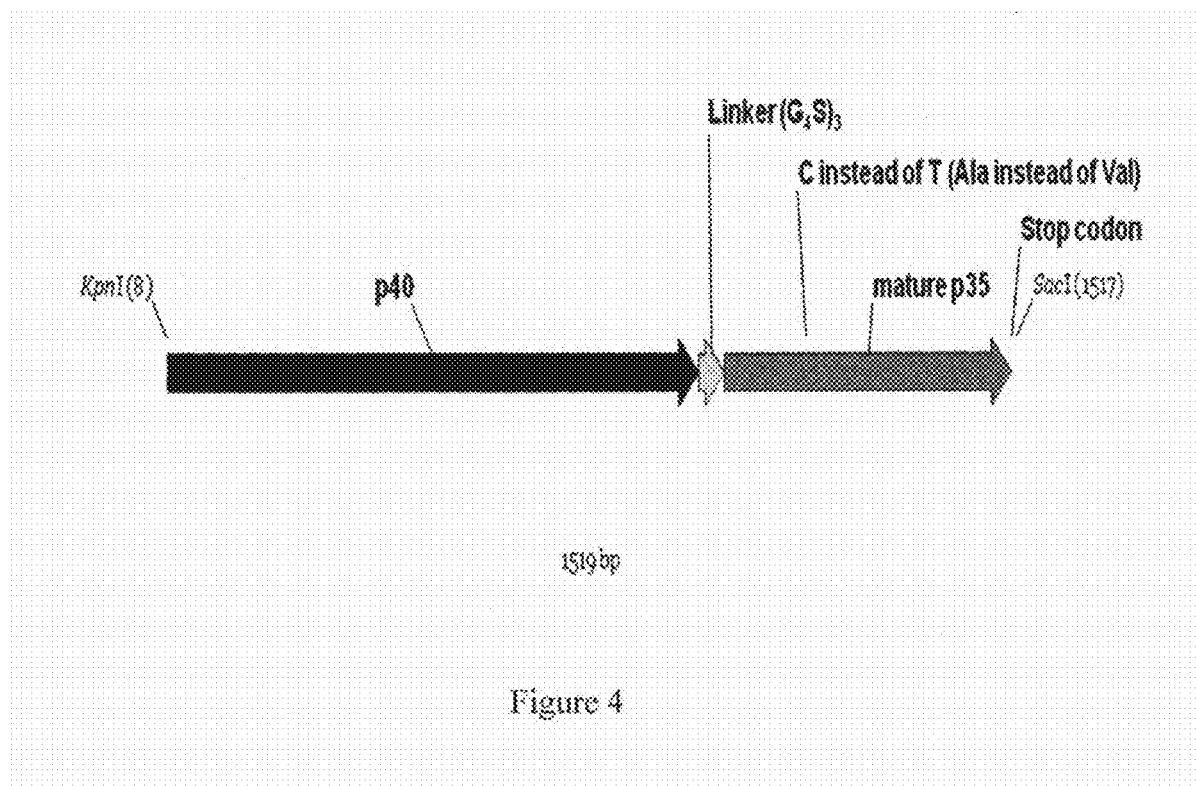
FIG. 4 depicts a ChIL-12 gene construct—coding region.
Figure 5:
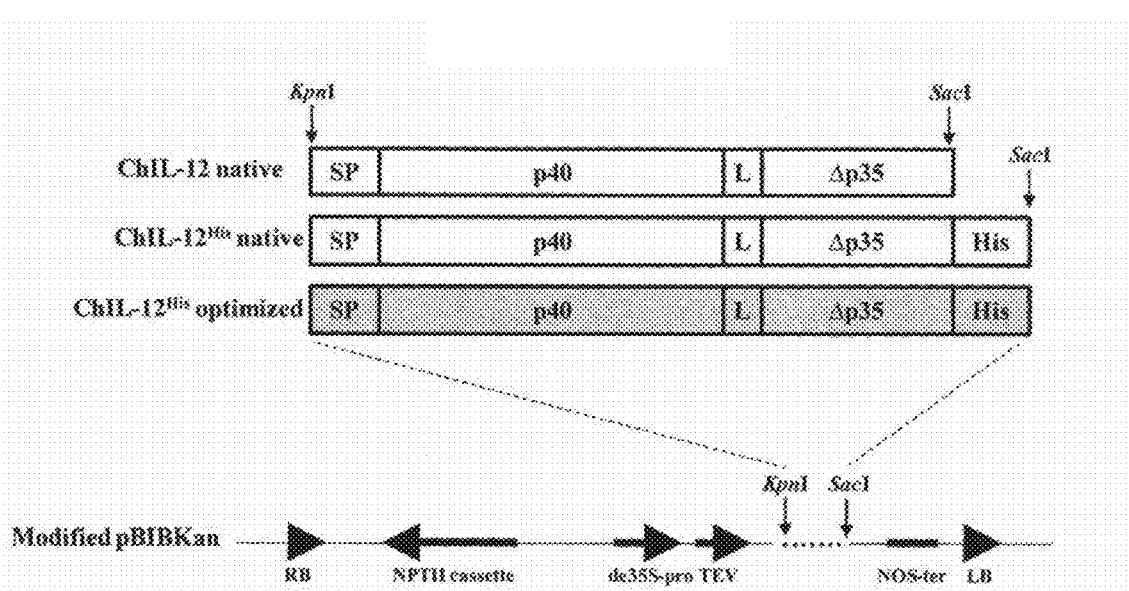
FIG. 5 depicts the T-DNA region of vectors developed for *Agrobacterium*-mediated transfer of the chIL-12 gene into plants.
Figure 6:
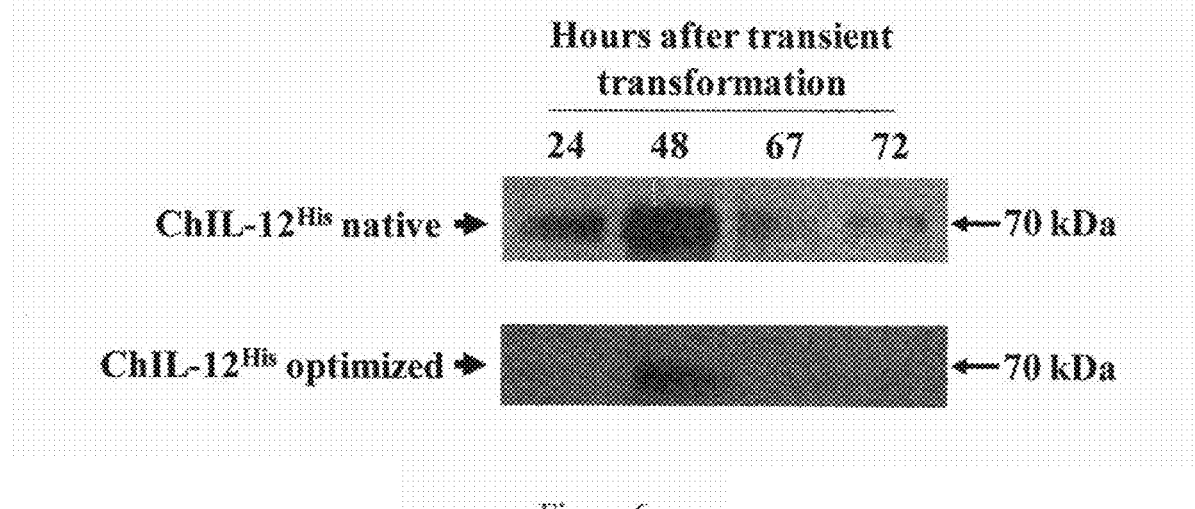
FIG. 6 depicts a time course analysis of ChIL-12$^{His}$
Figure 7:
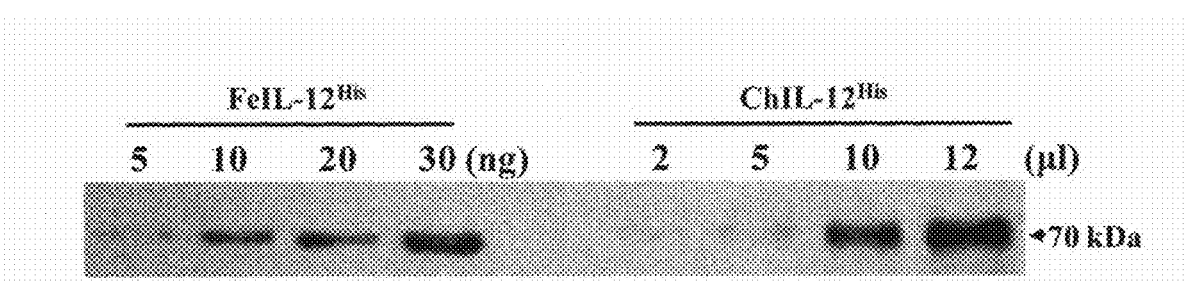
FIG. 7 depicts yield estimates of ChIL-12$^{His}$
Figure 8:
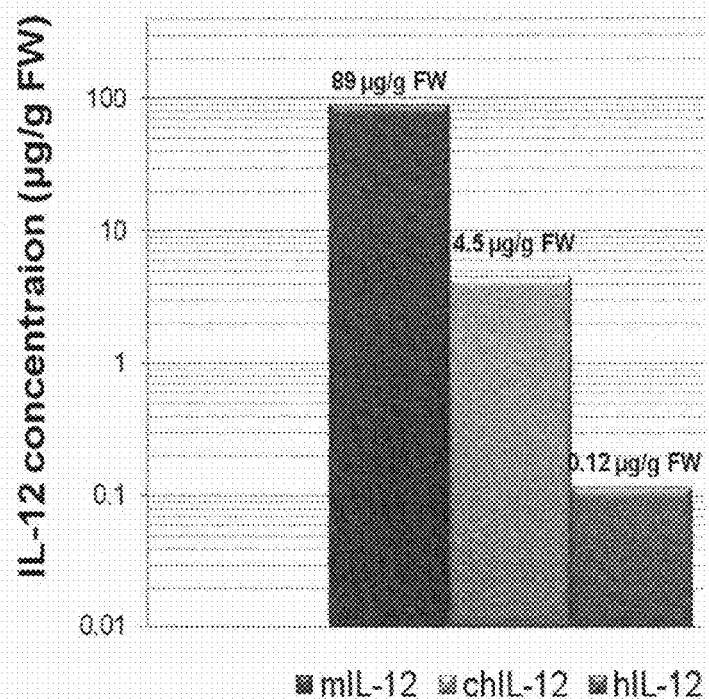
FIG. 8 is a comparison of yields of IL-12 from different species

FIGS. 1 through 3 depict yields of recombinant Interleukin-12 (IL-12) from closely related species are highly variable. Vectors encoding murine or human IL-12 were identical with the exception of the IL-12-encoding regions and represented either single-chain forms (subunits joined by a gly/ser linker) or vectors that encoded each subunit (p35 and p40) as distinct gene products. Analyses quantified the p70 heterodimeric product. These analyses used approaches described in Liu et al., 2008. J. Interferon Cytokine Res. 28: 381-392 and Medrano et al., 2009.

Expression of the transferred sequence can be checked by detecting the marker gene, and various methods including, for example, the northern blotting assay or RT-PCR with RNA recovered from cells, the ELISA assay or western blotting assay with an antibody of the expressed protein, or the detection of enzyme activity in the culture medium or cells in case of the protein being an enzyme.

The product of the sequence expression may or may not be isolated at this point. There are a variety of means available to one skilled in the art for purification of such products so expressed and any may be employed in the invention. For example, one could employ fractionation with affinity, immunoaffinity or ion exchange columns; ethanol, PEG, or ammonium sulfate precipitation; reverse phase HPLC; chromatography with cation exchange resins such as silica or DEAE, e.g. gel electrophoresis with Sephadex G-75; or chromatography with a plasminogen column to which the target product is linked. These methods can be referred to, for example, *Guide to Protein Purification Methods in Enzymology*, vol. 182, edited by Deutscher, Academic Press.

The following examples are offered by way of illustration and not by way of limitation. All references cited herein are incorporated herein by reference.

Example 1 Involves Transient Expression of ChIL-12$^{His}$ Constructs in *Nicotiana benthamiana* Leaves to Assess Yield Potential and Bioactivity of Recombinant Products Development of ChIL-12 Vectors for Expression in Plants.

In order to assess the expression levels of ChIL-12 in plants, one must compare yields from vectors that 1) incorporated the native chicken sequences or 2) used a synthetic DNA sequence based on tobacco codon usage and reduced mRNA AG. For both constructs, DNA sequences included the complete chicken IL-12p40 coding sequence (including the chicken p40 signal peptide), an in-frame linker sequence encoding 15 amino acids [$(Gly_4Ser)_3$], the mature ChIL-12p35 coding sequence (i.e., without the p35 signal peptide), sequences encoding 6 histidines and a stop codon, and appropriate flanking restriction endonuclease sites. These sequences were synthesized, introduced into bacterial cloning vectors, and fully sequenced prior to mobilization into plant expression vectors. Both genes ("native" and "tobacco codon optimized") should produce an identical histidine-tagged single-chain chicken IL-12 product. The ChIL-12 sequences were introduced into a modified pBIB-Kan vector (Becker, 1990) that provided a strong constitutive promoter and translational enhancer (de35S/TEV), termination/polyadenylation signals, an adjacent NPTII selectable marker (kanamycin resistance), and the right and left border sequences that delineate the T-DNA region transferred into plant cell during *Agrobacterium*-mediated transformation as shown in FIGS. 4 and 5.

SEQ ID NO. 1 is an example of chicken IL-12 native nucleic acid sequence (chIL-12 native), and SEQ ID NO. 2 is the analogous coding region comprising a synthetic sequence developed using tobacco codon preferences and optimized for reduced "delta-G" (chIL-12 optimized).

FIGS. 4 and 5 show components of constructs used to transform/transfect tobacco. FIG. 4 depicts the ChIL-12 gene construct—coding region with p40, sequence encoding p40 subunit of chIL-12 including the signal peptide; mature p35, sequence encoding the p35 subunit of chIL-12 without the signal peptide; 6×HIS, sequence encoding six histidine residues. FIG. 5 depicts the T-DNA region of vectors developed for *Agrobacterium*-mediated transfer of the ChIL-12 gene into plants. As demonstrated in the figures, RB, right border; NOS-ter, terminator 3'NOS; 6×His, 6 histidine epitope tag; native ChIL-12 p40-L-p35, chicken interleukin-12 p40 subunit-Linker[$(G_4S)_3$]-p35 subunit; TEV, tobacco etch virus enhancer; de 35S-pro, double-enhanced 35S promoter; NOS-pro; promoter NOS; NPTII, neomycin phosphotransferase gene; LB, left border; ChIL-12 optimized p40-L-p35, codon optimized version of ChIL-12 p40-L-p35.

Expression of ChIL-12 in Tobacco Leaves Comparing Native and Tobacco Codon-Optimized ChIL-12 Sequences.

An optimized *Agrobacterium*-mediated transient expression system that permits rapid assessment of plant-synthesized product (Medrano et al., 2009) was used. In this system, activated cultures of *A. tumefaciens* carrying IL-12 constructs are infiltrated into intact leaves of the "wood" tobacco, *Nicotiana benthamiana*. Under these conditions, *A. tumefaciens* initiates infection and transfers its T-DNA region into plant cells supporting several rounds of transcription/translation independent of integration into the plant genome. Inoculated leaves are harvested at 48 to 96 hours post infiltration depending on construct/product. This transient system was used 1) to determine product yields of chicken IL-12 compared to the high-expressing mouse IL-12 construct and low-expressing human IL-12 gene; 2) to assess whether codon usage variants affect product yield; 3) to produce material for developing analytic tools for ChIL-12 detection and quantification; 4) to optimize extraction buffers and initial purification steps; and 5) to develop ChIL-12 product at sufficient yield and purity for IL-12 bioactivity assays on primary chicken splenocytes. For transient expression, the plant expression vectors for ChIL-$12^{His}$ described above were introduced into *A. tumefaciens* strain LBA4404 for transient expression in *N. benthamiana.*

To establish which time point yields the greatest amount of recombinant ChIL-$12^{His}$ product, leaves were harvested 24, 48, 67, and 72 hours post agro-infiltration. Crude protein extracts from these leaves were subjected to SDS-PAGE and western immunoblot analysis to assess yields. As shown in FIG. 6, 48 hours post infiltration appears to yield maximum recovery of the 70 kDa ChIL-12 product. Results in FIG. 6 also compare product yields from leaves processed in parallel that used either the "native" chicken DNA sequences or a synthetic sequence based on tobacco codon usage ("optimized"). Surprisingly, it appears that the native chicken sequences provide significantly greater yields of ChIL-12 when expressed in tobacco leaves compared to the tobacco-codon optimized as shown in FIG. 6. Based on these results, subsequent analyses have focused exclusively on products developed using the "native" ChIL-12 sequence.

FIGS. 6 through 8 depict characterization of ChIL-$12^{His}$ produced in leaf. FIG. 6 shows that time course experiment of native and codon-optimized ChIL-$12^{His}$ was performed. *Nicotiana benthamiana* leaves were vacuum infiltrated with *Agrobacterium* bearing the ChIL-$12^{His}$ expression vectors (t=0) and leaves were harvested at times indicated. Proteins from crude extracts were separated by SDS-PAGE and subjected to Western immunoblotting using anti-6×-His antibodies. p70 product yields for both native and codon-optimized ChIL-$12^{His}$ reached a maximum at 48 hours. FIG. 7 is an estimation of ChIL-$12^{His}$ yields at 48 h post-infiltration. A densitometric analysis of the bands of the western blot allowed semi-quantification. A 6×His-tagged feline (Fe) IL-12 of known concentration was run simultaneously and used to establish a standard curve. Results indicate the inventors yield of recombinant ChIL-$12^{His}$ after 48 hours of transient expression is 4.5 μg/gram of fresh tissue. FIG. 8 is a comparison of yields of IL-12 from different species (mouse, chicken, and human IL-12) transiently expressed in *N. benthamiana* leaves (note log scale).

In order to estimate the yields of ChIL-12, the inventors utilized a semi-quantitative densitometric analysis of western blot bands as shown in FIG. 7. Known concentrations of feline IL-12 were run simultaneously and used to plot a standard curve. Both the chicken IL-12 and feline IL-12 contain a 6×HIS tag permitting direct comparisons using an anti-HIS antibody for detection. Based on this analysis, the inventors estimate that the yield of recombinant ChIL-$12^{His}$ after 48 hours of transient expression is approximately 4.5 μg/gram of fresh tissue as shown in FIG. 7. In previous experiments, they had demonstrated that mouse IL-12 is very effectively produced in tobacco whereas the human IL-12 shows almost a 1000-fold lower expression using identical vector components and expression conditions. These are closely related homologs (e.g., murine IL-12 interacts with human IL-12 receptors and stimulates human splenocytes). Thus, it is not possible to predict or anticipate whether the levels of IL-12 from a particular species (human vs. mice vs. avian) will successfully accumulate in plant cells and tissues. As shown in FIG. 8, ChIL-12 shows intermediate expression—yields are ~40 times greater than human IL-12, but ~20-fold lower than mIL-12. Most importantly, however, the yields of ChIL- 12 are consistent with moving forward for bioactivity assessment and for commercial development.

Purification and Characterization of Plant-Synthesized ChIL-12.

As a first step toward bioactivity testing, the inventors developed a quick two-step FPLC (Fast Protein Liquid Chromatography)-based purification protocol for recovery of the HIS-tagged ChIL-12. Infiltrated leaves were homogenized with 50 mM phosphate column-equilibration buffer (1:2 weight:volume), centrifuged, and filtered through miracloth. The diluted filtered medium was then loaded onto UNO-sphere S cation-exchange chromatography columns. After a wash step with equilibration buffer, ChIL-12$^{His}$ was eluted from the column with a solution containing 500 mM sodium chloride; 50 mM phosphate buffer. The S-column eluate was loaded onto equilibrated Ni-NTA His-Binding Superflow resin and washed with equilibration buffer (300 mM NaCl, 50 mM phosphate buffer, 10 mM imidazole). ChIL-12$^{His}$ was eluted from the column with equilibration buffer containing 500 mM of imidazole and concentrated by ultrafiltration using Centricon columns YM-30 and stored at −20° C. The inventors' goal in this procedure was to develop a product of sufficient purity to support bioactivity assays on chicken splenocytes.

Figure 9:
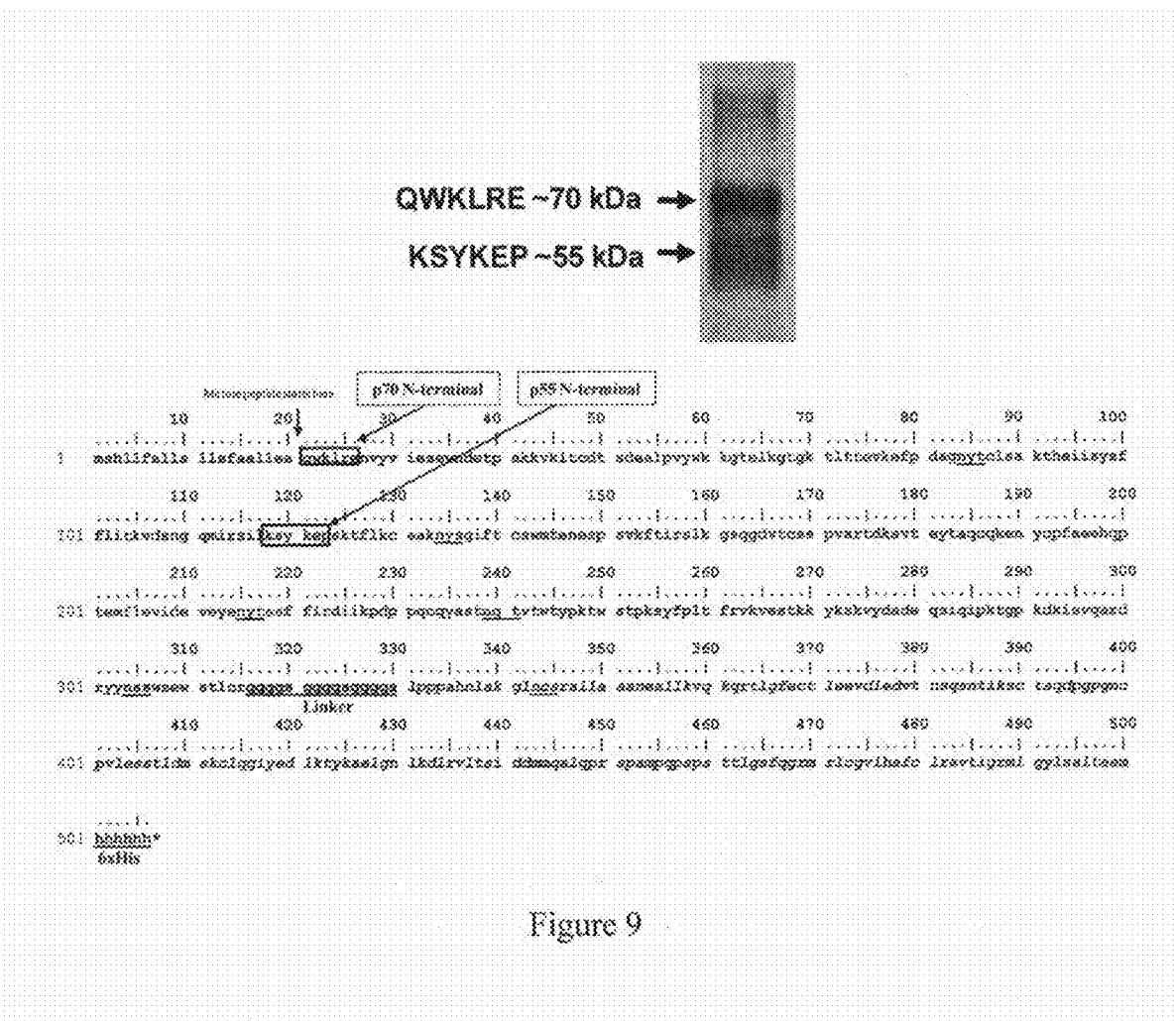
FIG. 9 depicts an N-terminal sequencing of tobacco-synthesized ChIL-12$^{His}$

In order to characterize the tobacco-synthesized ChIL-12$^{His}$ product, two western blotting procedures were designed and standardized: i) Western blot using anti-6×-His (C-term)-AP conjugated antibody made in mouse (dilution 1:2000) and ii) Western blot using anti-feline IL-12/IL-23 p40 polyclonal made in goat (dilution 1:500). Western analyses of initial purified ChIL-12 preparations revealed products of two molecular sizes (~70 and ~55 kDa) as seen in FIG. 9 (SEQ ID NO 3). These products cross-reacted with both anti-HIS and anti-Feline IL-12p40 antibodies and were not present in control tobacco extracts produced from leaves infiltrated with *A. tumefaciens* bearing "empty vector" (data not shown). ChIL-12 is a glycoprotein and the predicted size of the protein without glycan modification is 56,285 Daltons. The inventors reasoned that the lower molecular weight product could be a non-glycosylated form or represent a degradation product. To distinguish between these possibilities, they subjected the purified 70 kDa and 55 kDa products to N-terminal sequence analysis. The p70 product showed the expected amino terminus (QWKLRE . . . ) indicating precise cleavage of the chicken signal peptide. The lower band (~55 kDa) yielded an N-terminal sequence of KSYKEP suggesting that it is a degradation product lacking the N-terminal 97 amino acid residues as shown in FIG. 9 (SEQ ID NO 3). These analyses confirm that the tobacco synthesized and purified product is in fact chicken IL-12. Subsequent analyses indicated that the degradation event occurs during extraction. Initial steps to optimized tissue extraction conditions have reduced this cleavage event and enhanced full-length product recovery.

FIG. 9 (SEQ ID NO 3) shows the N-terminal sequencing of tobacco-synthesized ChIL-12p70 and 55 kDa degradation product.

Bioactivity Assessment of Plant-Synthesized ChIL-12.

Figure 10:
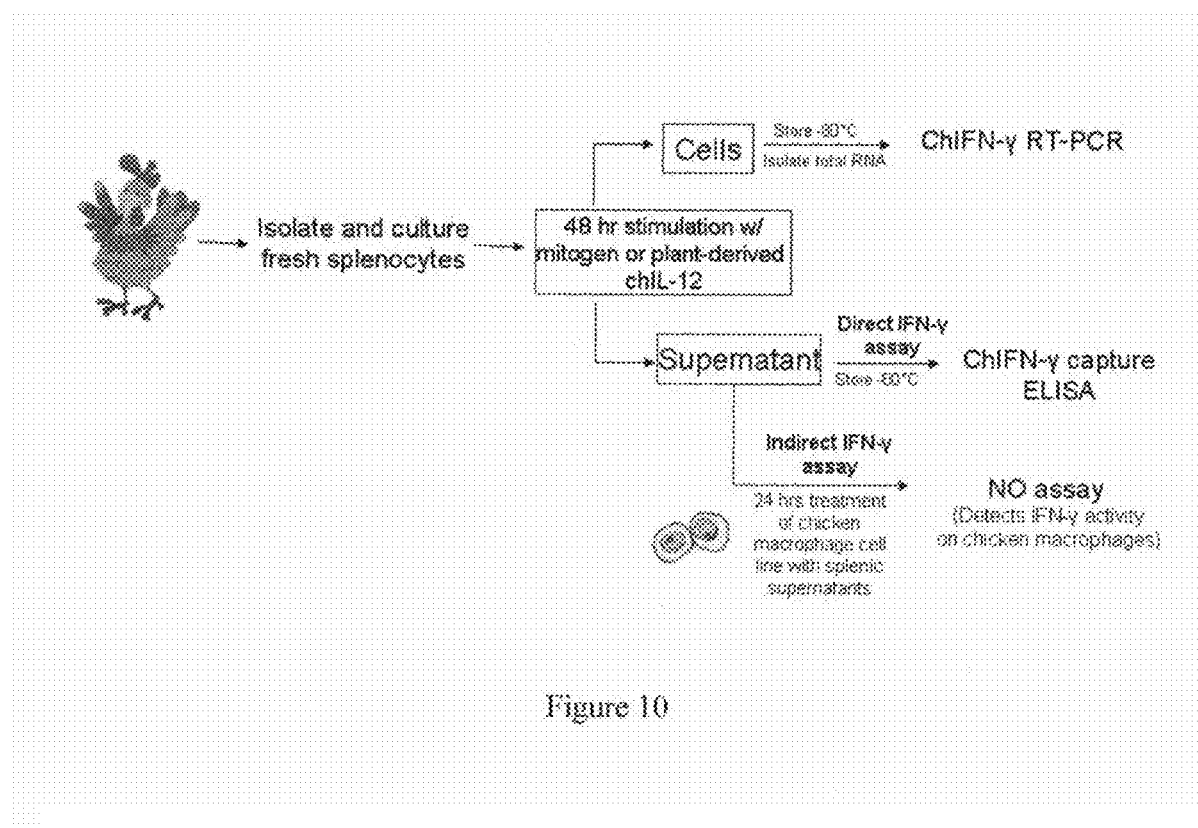
FIG. 10 depicts a ChIL-12$^{His}$ bioassessment strategy.

Paramount to establishing the feasibility of this project, the inventors have successfully confirmed the bioactivity of their plant-derived ChIL-12 product. It is well documented in mammals that induction of the critical T lymphocyte-mediating cytokine, interferon-gamma (IFN-γ), is a hallmark response of IL-12 activity. Therefore, the bioactivity of their recombinant ChIL-12 was assayed in vitro based on the induction of splenic ChIFN-γ. Due to the less developed tools for chicken immune characterization relative to mammalian systems, they used a multipronged strategy that involved both direct and indirect detection of ChIFN-γ in establishing the functionality of their ChIL-12 product as shown in FIG. 10. FIG. 10 is a ChIL-12$^{His}$ bioassessment strategy. ChIFN-γ was assayed by 3 different methods: 1) ChIFN-γ ELISA; 2) an indirect assay based on ChIFN-γ-mediated NO release by a chicken macrophage cell line; and 3) ChIFN-γ RNA levels determined by realtime-quantitative RT-PCR Standard IL-12 activity assays measure the stimulation of interferon gamma (IFN-γ) production in immune-responsive cells. The initial bioassessment of the inventors' ChIL-12 was conducted at the University of Arkansas' Center of Excellence for Poultry Science in collaboration with Dr. Gisela Erf, a poultry immunologist. Briefly, spleens were isolated from three 11-week-old male, Light Brown Leghorn chickens (MHC B101 homozygous line). These birds were maintained and handled in accordance with protocols approved by the University of Arkansas Animal Care Committee (approval #05009). Each spleen was processed and analyzed independently according to standard Erf laboratory protocols (see Bowen et al., 2006a; 2006b) and the resulting splenocytes were grown in RPMI 1640 at 41° C. in 5% $CO_2$ humidified atmosphere. Cells were plated in triplicate, at a density of $10^7$ cells/ml, on either 96-well (for protein-based assays) or 12-well (for RNA-based assay) microtiter plates. Splenocytes were incubated with serial dilutions of 1) plant-derived ChIL-12; 2) similarly treated purification fractions from leaf material expressing the "empty" vector (mock); 3) media (negative control); and 4) mitogen (ConA and LPS; positive controls) for 48 hours.

Figure 11:
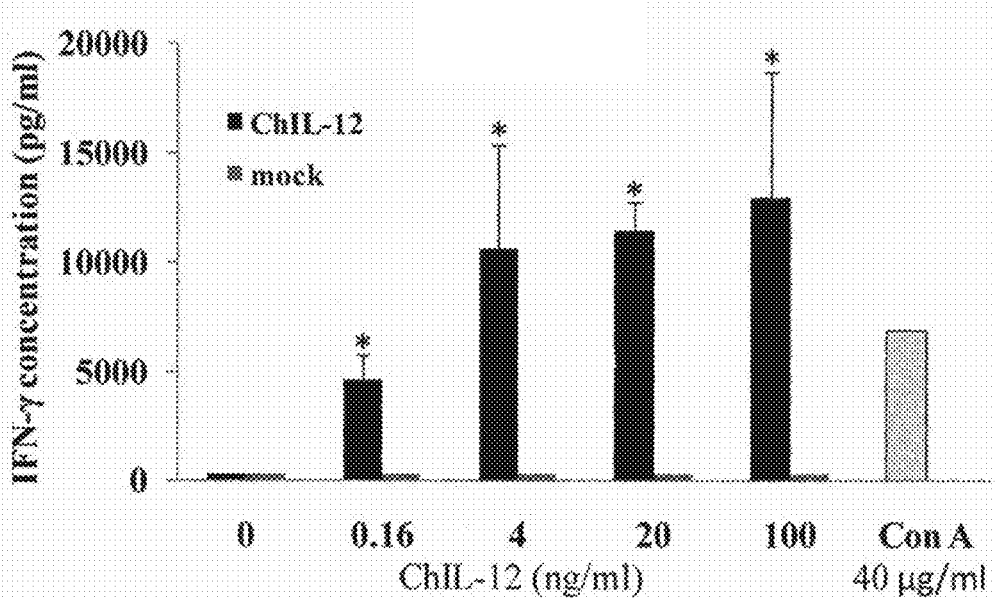
FIG. 11 depicts ChIFN-γ detection by ELISA in chicken splenocyte cultures after ChIL-12$^{His}$ treatment.
Figure 12:
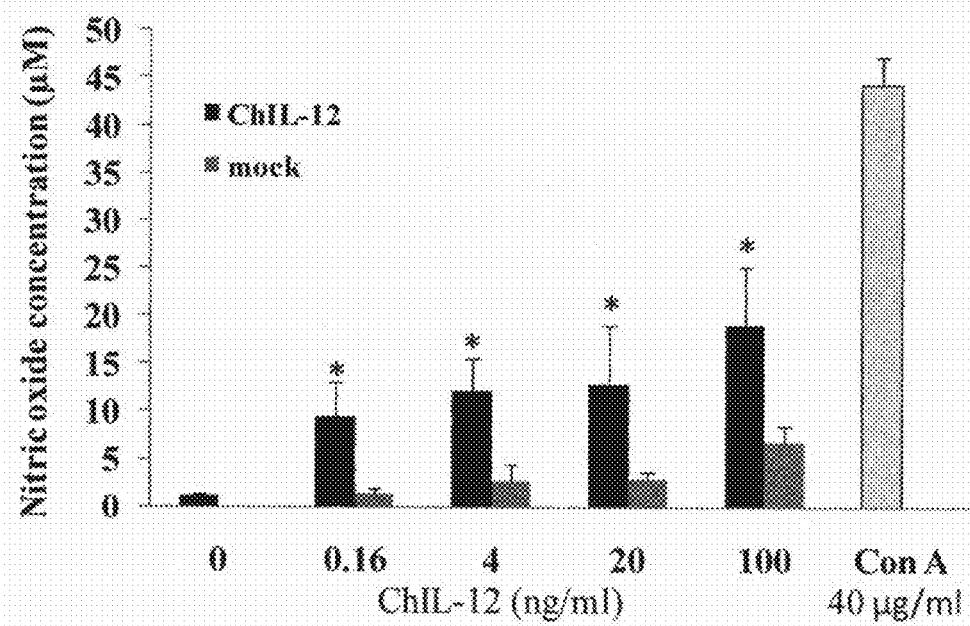
FIG. 12 depicts ChIFN-γ detection by an indirect NO assay in chicken splenocyte cultures after ChIL-12$^{His}$ treatment.
Figure 13:
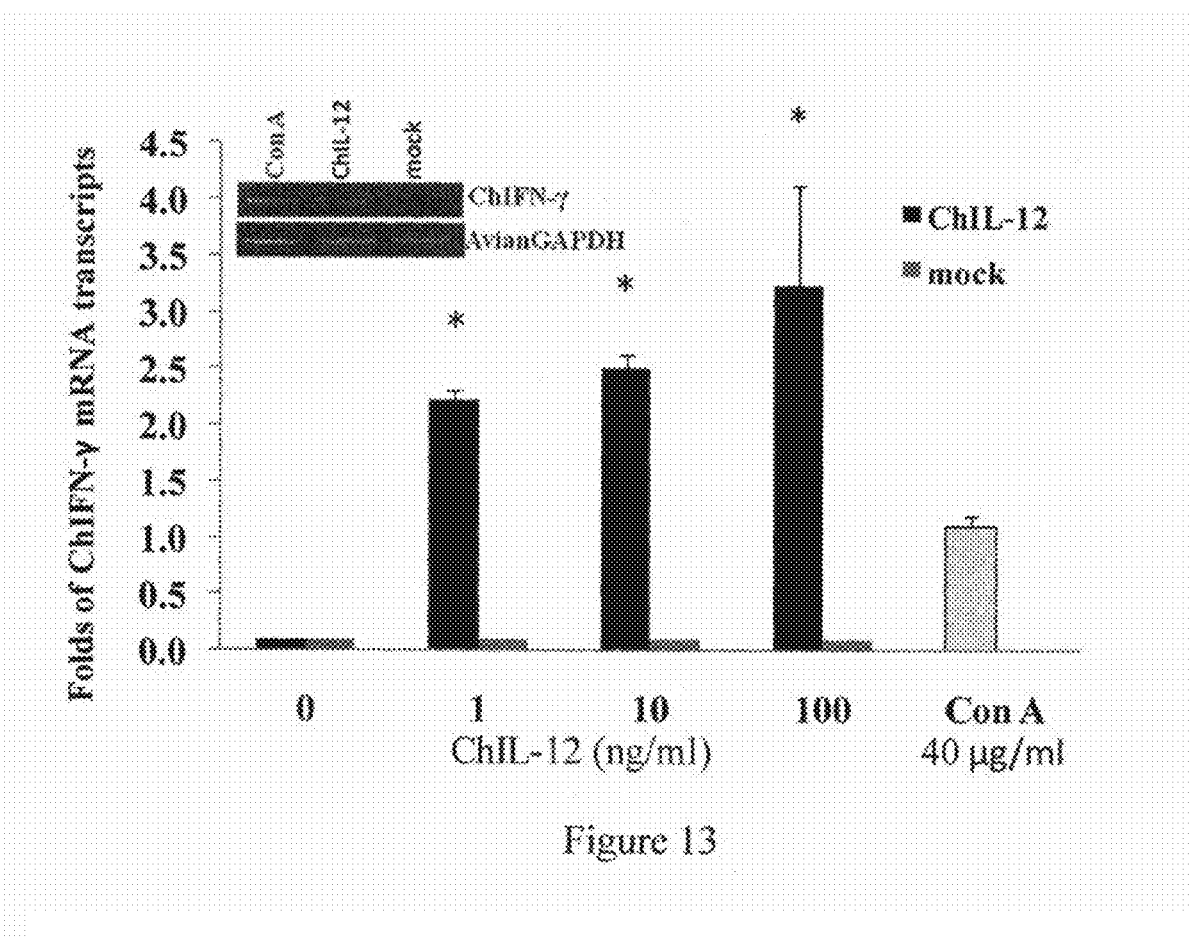
FIG. 13 depicts detection of ChIFN-γ transcripts in chicken splenocyte cultures after ChIL-12$^{His}$ treatment.

Recent success in expressing functional ChIFN-γ in a baculovirus production system (Lambrecht et al., 1999) and concomitant production of monoclonal antibodies (Lambrecht et al., 2000) has resulted in a newly available commercial ChIFN-γ capture ELISA kit (Invitrogen; Cat# CAC1233). This ELISA enabled the inventors to directly measure secreted ChIFN-γ in the media of 48 hour-treated chicken splenic cultures. As shown in FIGS. 11 through 13, the inventors' plant-derived ChIL-12 elicited strong induction of ChIFN-γ. The expected IL-12 dose-dependent effect on IFN-γ secretion of mammalian splenocytes (e.g. Liu et al., 2008) was mimicked in chicken splenocytes cultured with plant-derived ChIL-12. In addition, picogram levels of recombinant ChIL-12 were effective at eliciting a similar IFN-γ stimulatory response mediated by the classic T-cell mitogen, concanavalin A (ConA).

FIG. 11 shows ChIFN-γ detection in chicken splenocyte cultures after ChIL-12$^{His}$ treatment. It further shows chicken splenocytes were stimulated in triplicate with serial dilutions of ChIL-12$^{His}$ (0-100 ng/ml) and mock (0-100 ng/ml). After 48 hours of incubation at 41° C., 5% $CO_2$, supernatants were collected and tested for ChIFN-γ levels by ELISA assay. FIG. 12 shows that these supernatants were subsequently used to stimulate macrophage-like chicken cell lines which were assayed for secretion of nitrogen intermediates such as NO. FIG. 13 shows ChIFN-γ mRNA transcript (308 bp) levels in splenocytes relative to the avian GAPDH housekeeping gene (172 bp). This analysis was done by real-time quantitative RT-PCR. The ability of plant-derived ChIL-12$^{His}$ to induce ChIFN-γ transcript and protein in chicken splenocytes was compared with the T cell stimulant Concanavalin A (40 μg/ml), and a mock (product of analogous purification fractions from leaves expressing an empty vector) as a negative control. Data are representative of at least three independent experiments; mean±SD. *Significantly different from mock based on ANOVA Tukey's Multiple Comparison Test and t-test, $p<0.05$.

The original functional characterization of ChIL-12 by Degen and colleagues (2004) employed an indirect assay for determining ChIFN-γ levels. The inventors therefore carried out this same Nitric Oxide (NO) assay with chicken splenocytes that allowed comparison of their ChIL-12 activity levels to those reported in this previous study. In the NO assay, the presence of ChIFN-γ in the supernatant of IL-12-stimulated chicken splenocytes was quantitated based on the ability of the supernatant to subsequently stimulate macrophage-like chicken cell lines to secrete nitrogen intermediates such as nitric oxide (NO). As IFN-γ is the major macrophage-activating factor in chicken, NO release (measured via the Griess reaction) is accepted as a surrogate of IFN-γ production. Unlike the inventors' splenocyte activation assays which utilized purified and quantified ChIL-12, the original ChIL-12 bioactivity assessment done by Degen et al. (2004) used titrated crude extracts from ChIL-12-expressing COS cells, which undermines direct quantitative comparisons with the present inventors' plant-derived ChIL-12 results. However, when comparing the non-toxic dose range (based on proliferation assays) of Degen's crude extracts, the present inventors' NO assay results with recombinant ChIL-12 show a similar dose-dependent trend. In comparing the inventors' results with the indirect NO assay and ChIFN-γ ELISA response curves to plant-derived ChIL-12, the ELISA-based assay is more streamlined and reproducible and will be the method of choice for future QA/QC of the inventors' ChIL-12 products. Finally, total RNA from coordinately treated splenocytes was isolated to quantify ChIFN-γ mRNA levels in treated splenocytes by RT PCR. This analysis confirmed induction of ChIFN-γ expression by plant-derived ChIL-12.

As described above, plant-derived ChIL-12 activated IFN-γ synthesis in in vitro studies. In order to further demonstrate IL-12 activities in vivo, immune stimulation was assessed in chickens treated with plant-derived ChIL-12. Studies involving parenteral delivery of ChIL-12 were used in validating ChIL-12 activity in a whole animal model as well as establishing toxic doses and serum half-life of our recombinant ChIL-12. Experiments similar to those designed in evaluating mammalian IL-12 in vivo activity (Marinaro et al., 1999; Arulanandam et al., 1999) were designed for assessing our ChIL-12 in chickens. ChIL-12 was co-delivered via interperitoneal injection with Freund's Complete adjuvant in one day old chickens and shown to induce serum IFN-γ induction within 24 hours. These experiments provided validation that the inventors' plant-derived chicken IL-12 exhibits full biological activity in the target organism.

As described above, the feasibility of using plant-based bio-production for commercial bioactive chicken IL-12 has been demonstrated. The inventors have developed and tested multiple ChIL-12 gene constructs for effective expression in plants. They have selected a His-tagged native ChIL-12 construct that provides reproducible product yields at levels that support scale-up for vaccine trials and commercial product development for the research reagent market. Most importantly, they have demonstrated that this plant-synthesized product shows excellent bioactivity in mediating the signature IL-12 read-out, induction of splenic synthesis and secretion of interferon-γ.

Example 2 Demonstrations that ChIL-12 Lacking the HIS-tag is Effectively Produced in Plants and Fully Active The bioactive ChIL-12 developed and characterized in experiments described above (Example 1) represents a 6×HIS-tagged version. The inventors were very encouraged to find that this tagged version shows strong bioactivity because the presence of the tag provides significant purification and detection advantages. Whereas the presence of a "non-native" epitope tag could raise regulatory issues for human vaccine applications, discussions with researchers in the poultry vaccine development arena suggest that the HIS-tag is unlikely to be an issue for poultry applications. The HIS-tag is not expected to negatively impact ChIL-12 activity. To test this, the ChIL-12 sequence was re-engineered without the 6×-his tag.

Construction of ChIL-12 Gene Lacking the HIS-Tag.

Briefly, an intermediate pBC cloning vector containing the "native" single-chain ChIL-12 (p40-linker-p35) with a C-terminal 6×-HIS-tag was used as a PCR template to modify the 3' end of the gene and facilitate subcloning. The following primers were used to introduce a 5'-KpnI and a 3'-stop codon and flanking SacI restriction site:

5'-GCGGTACCATGTCTCACCTGCTATTTGC-CTTACTTTCATTAC-3' (SEQ ID NO 4) and

5'-CGGAGCTCTTACATCTCTGCAGT-GAGGGCACTCAGGTAGCCC-3' (SEQ ID NO 5).

The ChIL-12 p70 fragment lacking the HIS-tag was subcloned and sequenced to confirm that no errors were introduced by PCR. This sequence was introduced into the pBIB-Kan plant transformation vector (which provides the double-enhanced 35S promoter, TEV enhancer and plant termination signals) and the vector mobilized into *A. tumefaciens* strain LBA4404 for transient expression in *N. benthamiana* leaves as described above. ChIL-12 with and without the HIS-tag were expressed in the transient leaf assay, harvested at 48 hours post-infiltration and frozen for subsequent processing. Comparative levels of ChIL-12 produced in leaves expressing either the HIS-tagged ChIL-12 (ChIL-12$^{His}$) or the ChIL-12 lacking the HIS-tag (ChIL-12$^{No-His}$) were compared by Western immunoblots of crude protein extracts.

Figure 14:
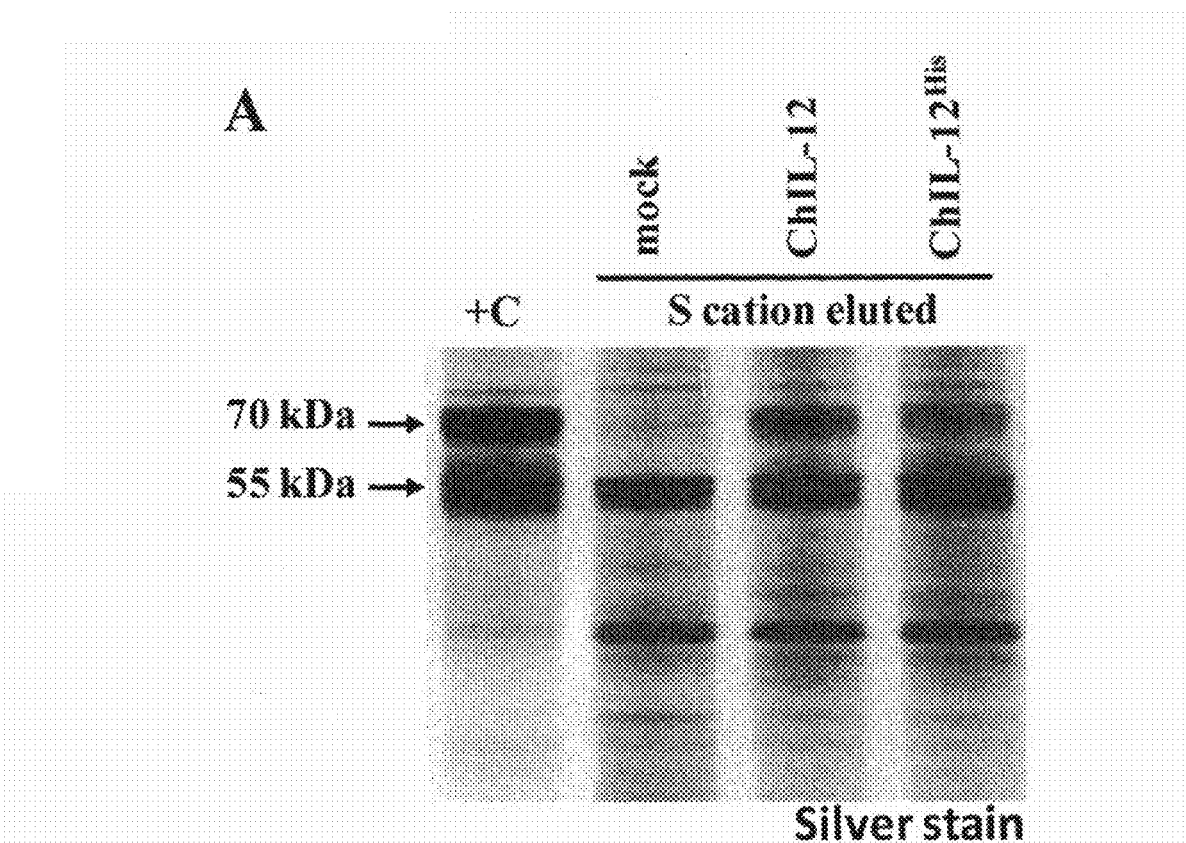
FIG. 14 depicts ChIL-12 with and without C-terminal His-tag following cation exchange chromatography.

In order to compare the bioactivity of ChIL-12 with and without the HIS-tag, the respective recombinant products were partially purified using a clean-up step followed by cation exchange chromatography (Unosphere S; Bio-Rad). Purity and yield was assessed by silver-stained PAGE analyses and ELISA. Bioactivity of purified ChIL-12 with and without the His-tag was compared using the splenic ChIFN-γ induction assay described above. As shown in FIG. 14, the bioactivity of chIL-12 with and without the HIS-tag was comparable.

Figure 15:
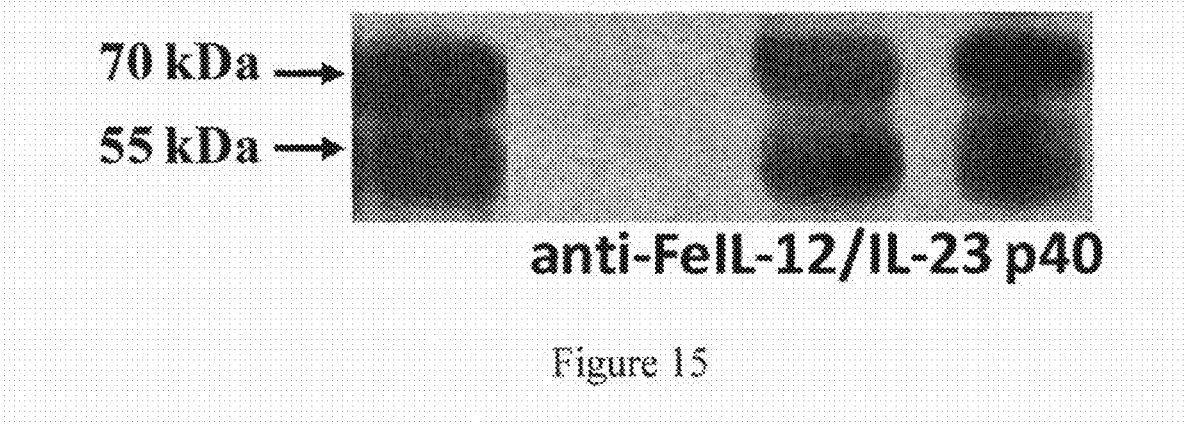
FIG. 15 depicts ChIL-12 with and without C-terminal His-tag on western immunoblots.
Figure 16:
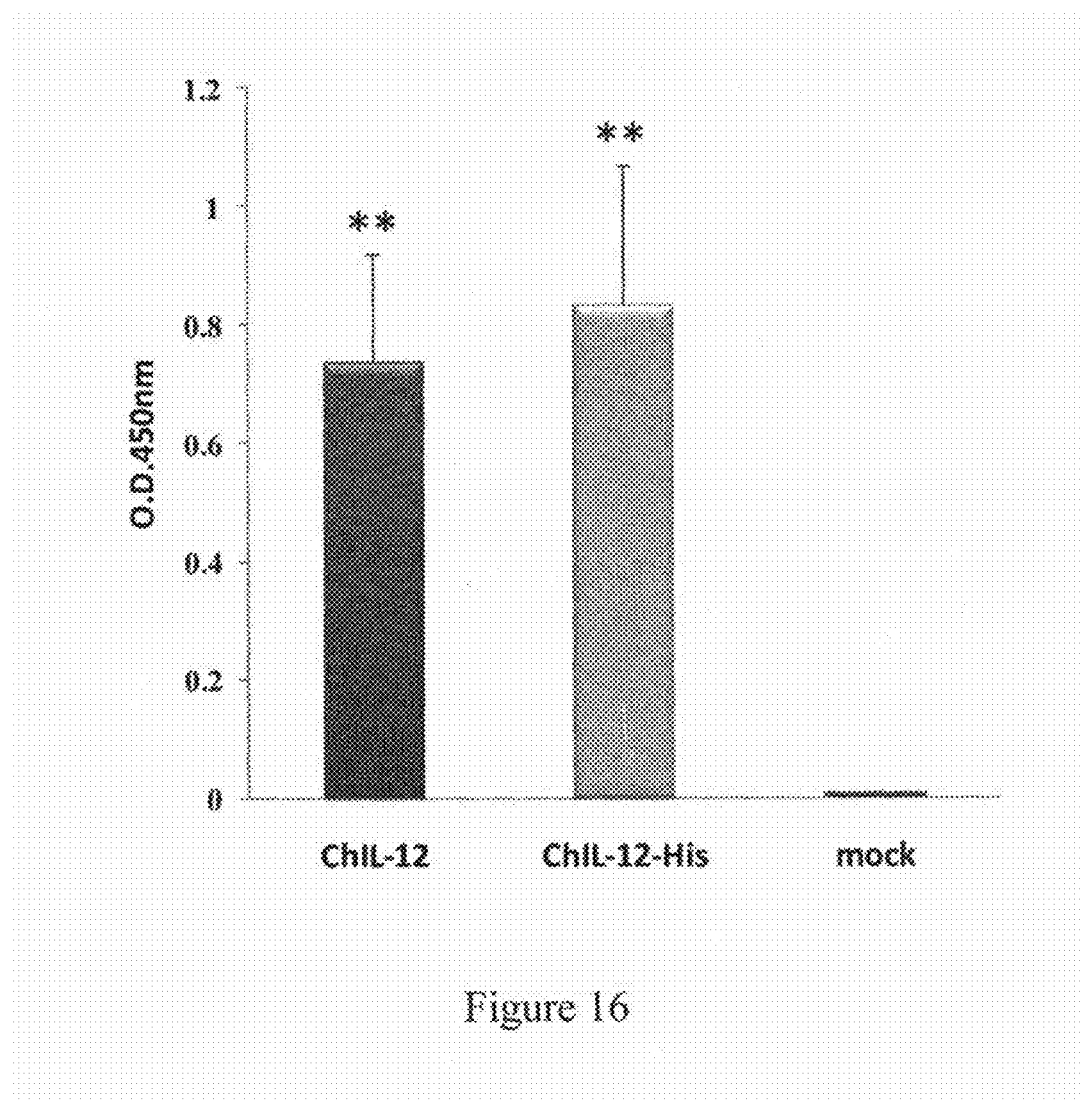
FIG. 16 depicts ChIFN-γ induction in chicken splenocyte cultures comparing ChIL-12 with and without C-terminal His-tag.

FIGS. 14 and 16 show ChIL-12 with and without C-terminal His-tag. FIG. 14 shows a silver stained SDS-PAGE comparing the positive control (+C; S cation chromatography/nickel resin purified ChM-12$^{His}$); mock (product of S cation chromatography purification from leaves expressing an empty vector); and ChIL-12 (without His-tag) and ChIL-12$^{His}$ eluted after S cation chromatography column. FIG. 15 is western blotting analysis detected with anti-FeIL-12/IL-23 p40 Ab comparing ChIL-12 and ChIL-12$^{His}$ following one step of purification (S cation eluted). FIG. 16 shows chicken splenocytes treated with 16 ng/ml of ChIL-12 variants (with or without the His-tag). Data are representative of at least three independent experiments; mean±SD. **ChIFN-γ induction different from mock-treated cells based on ANOVA Tukey's Multiple Comparison Test p<0.01.

Example 3 Demonstrates that ChIL-12 p35 and ChIL-12 p40 Co-Expressed in Plant Cells Assemble and are Bioactive As shown with human and mouse IL-12s, plants can also express and assemble IL-12 when each subunit is expressed from a distinct gene. This has been demonstrated in a transient expression system (Medrano et al., 2009) in the leaves of *N. benthamiana*. This is done either by expressing both genes from a single vector (e.g., as tandem genes), by co-delivery of two vectors into the same plant or tissue, or by generating independent transgenic lines that express the p35 subunit and the p40 subunit and subsequently crossing these plants to produce the heterodimer 70 kDa IL-12.

Expression Constructs for chIL-12 p3.5 and p40.

An intermediate pBC cloning vector containing the "native" single-chain ChIL-12 (p40-linker-p35) with a C-terminal 6×-HIS-tag was used as a PCR template. Primers were used to introduce a 5'-KpnI and a 3'-stop codon and flanking SadI restriction site for each fragment. The ChIL-12 p35 and p40 fragments were subcloned and sequenced to confirm the correct sequence. This sequence was introduced into the pBIB-Kan plant transformation vector containing the double-enhanced 35S promoter, TEV enhancer and plant termination signals; and the vector was mobilized into *A. tumefaciens* strain LBA4404 for transient expression in *N. benthamiana* leaves as described above. ChIL-12 with p35 sub-unit and p40 sub-unit were expressed in the transient leaf assay according to Medrano et al. (2009), and harvested at 48 hours post-infiltration.

Co-Expression of p35 and p40 Constructs in *N. benthamiana*.

While the majority of the inventors' studies expressing IL-12 in plants have utilized the single-chain coding sequence, the inventors successfully demonstrated that the molecular machinery of the plant in the context of a transient assay can effectively assemble subunits expressed on independent constructs in different *A. tumefaciens* strains to produce functional multimeric proteins. To test the utility of the plant transient expression system for co-expression and assembly of heterodimeric chIL-12, two individual *A. tumefaciens* strains, one harboring a p35 expression construct and the other coding for the p40 subunit of ChIL-12, were mixed in a ratio 1:1 prior to the infiltration step. The p70 IL-12 heterodimeric protein was successfully expressed and assembled with transient co-expression that is comparable to single-chain ChIL-12 expression. This transient system circumvents some of the hurdles associated with stable expression of independent subunit constructs that includes no need for multiple antibiotic selection and better matched subunit expression levels for driving stoichiometric assembly of the protein.

Product Characterization.

Crude extracts of leaves expressing each subunit and co-expressing both the p35 and p40 subunits were analyzed by western immunoblotting. The assembled p70 product was detected only in extracts from leaves expressing both subunit genes. Purified p70 product was quantified and used in chicken splenocyte activation assays (described previously) to confirm bioactivity.

Example 4 Demonstrates ChIL-12-Producing Seed as a Scalable, Low-Cost Source of Chicken IL-12 Immuno-Modulator and Vaccine Adjuvant—Tobacco Seed as a Model The inventors' transient expression system easily meets production requirements for research reagent markets, experimental material for vaccine trials and testing, and short-term "crisis management" of higher value birds (e.g., breeders, turkeys) in a HPAI outbreak. However, long-term strategies to address poultry industry vaccine markets pose scale and cost parameters incompatible with transient expression and extensive product purification. This example describes the development of stable transgenic tobacco lines that provides a scaleable source of bioactive ChIL-12 with the potential of direct oral efficacy in the absence of costly product purification.

Figure 17:
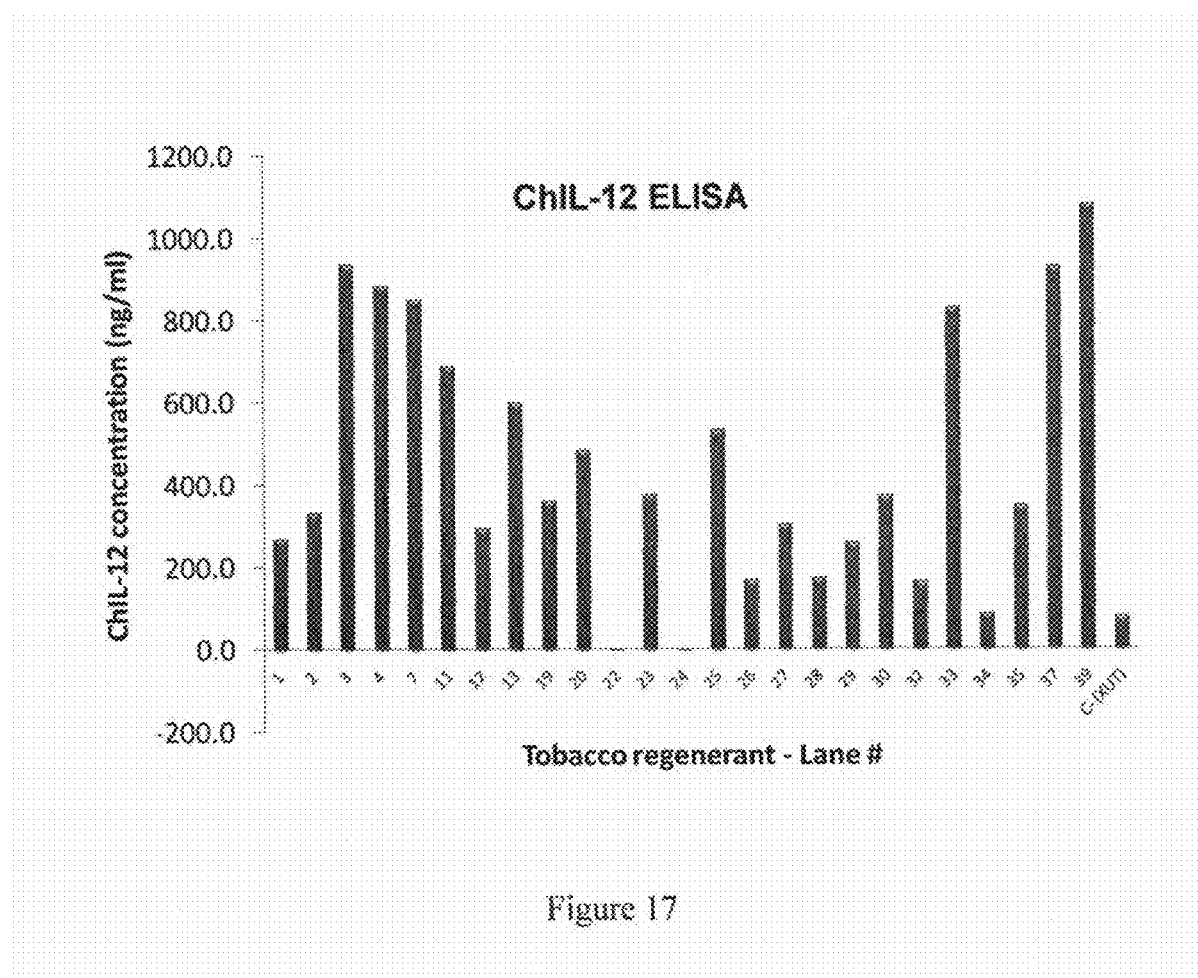
FIG. 17 depicts production of ChIL-12$^{His}$ in transgenic lines of *N. tabacum*.
Figure 18:
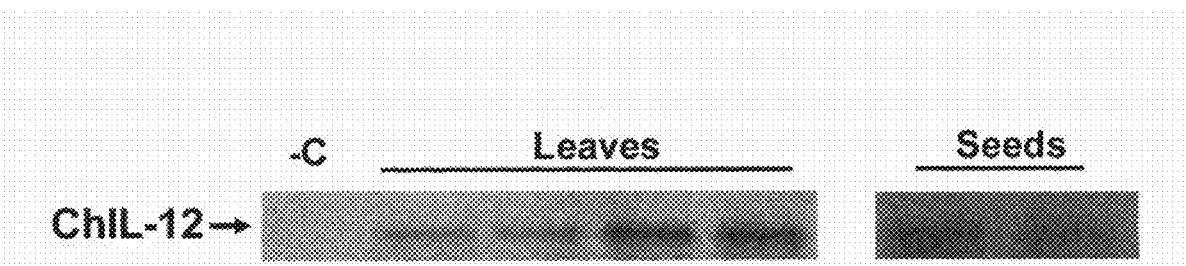
FIG. 18 depicts Western immunoblot analysis of ChIL-12$^{His}$ from transgenic tobacco leaves and seeds.

Stable transgenic tobacco (*Nicotiana tabacum*) lines were developed by standard *Agrobacterium*-mediated transformation methods as described (Medina-Bolivar and Cramer, 2004). The sequence and vector used were those described in Example 1. Plants containing the introduced sequences were selected based on kanamycin resistance (provided by the NPT II selectable marker adjacent to the chicken IL-12 gene in the transformation vector). Levels of chicken IL-12 in leaves of young kanamycin-resistant plants were measured by ChIL-12 ELISA as shown in FIG. 17. The five transgenic lines with the highest yields of chicken IL-12 were transferred to the greenhouse for seed production. First generations seed resulting from self fertilization of transgenic lines (representing a segregating population for the IL-12 transgenic events) were collected and analyzed for the presence of the chicken IL-12 product. As shown in FIG. 18, full-length 70 kDa IL-12 product is detected from crude protein extracts from both stable transgenic plants and from the seeds produced from these plants. This confirms that transgenic plants will produce and accumulate avian IL-12 product in seeds, a very useful storage and oral delivery vehicle for the avian cytokine.

FIGS. 17 and 18 demonstrate chicken IL-12 production in transgenic tobacco. FIG. 17 depicts leaves of a similar developmental stage were harvested from individual putative transgenic plants recovered from transformation and regeneration procedures. Leaves were processed as described for IL-12 extraction from *N. benthamiana* leaves and crude protein extracts used for ChIL-12 ELISA in order to quantify IL-12 levels (see Example 1). FIG. 18 depicts leaves from IL-12-expressing plant lines and pooled seed from these lines were extracted in SDS-PAGE gel sample buffer, and the cell-free extract used for SDS-PAGE and western immunoblot using a monoclonal anti-ChIL-12 (M8) made in mouse (dilution 1:500); a anti-mouse alkaline phosphatase conjugated was used as a detection antibody. Samples are as marked; an arrow indicates the 70 kDa ChIL-12$^{His}$ product.

Figure 19:
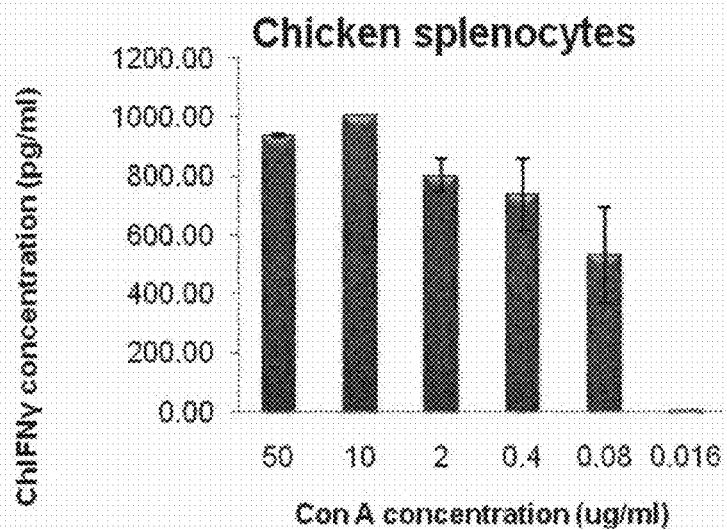
FIG. 19 depicts ChIFN-γ detection in chicken splenocyte cultures after concanavalin A treatment (positive control).
Figure 20:
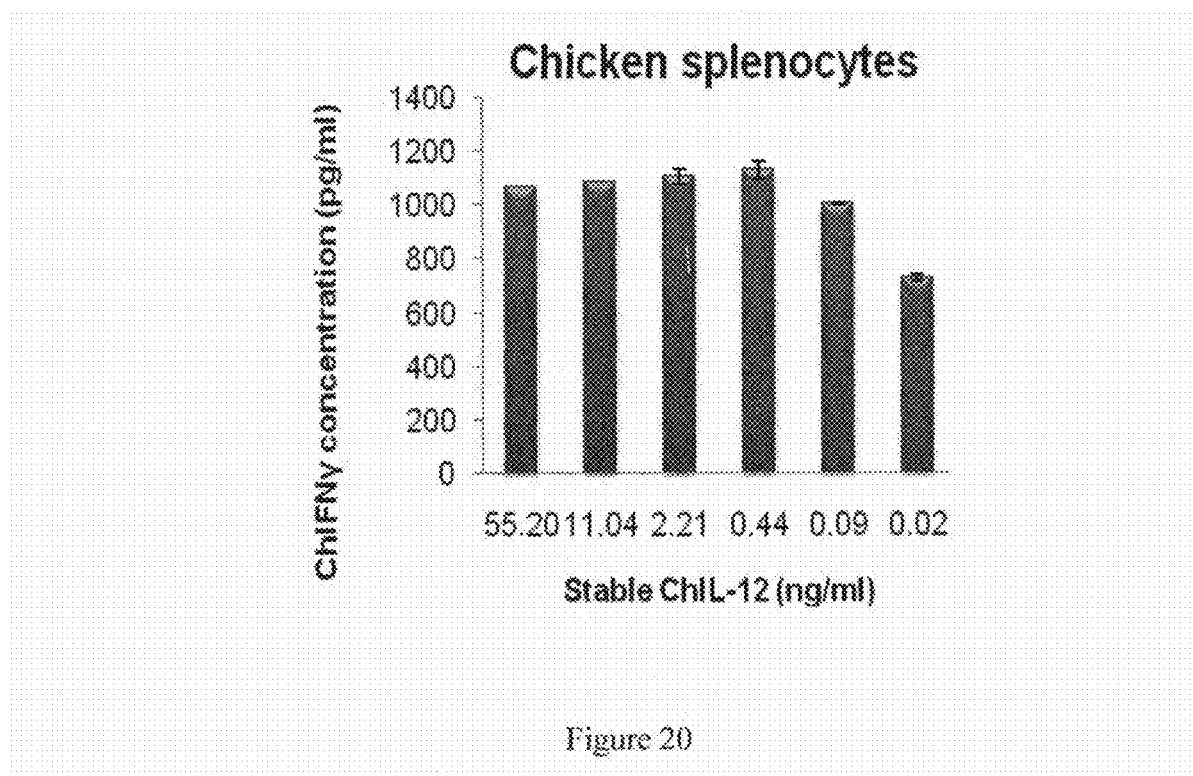
FIG. 20 depicts ChIFN-γ detection in chicken splenocyte cultures after treatment with ChIL-12$^{His}$ from transgenic lines of *N. tabacum* showing strong signature bioactivity in a dose-dependent fashion.

In order to demonstrate that the ChIL-12 produced in stable transgenic plants is bioactive, leaf material was harvested and ChIL-12 extracted and purified using protocols as described previously (Example 1 and Medrano et al, 2009). IL-12 was quantified by ELISA and used for the IL-12 bioactivity assay involving interferon-gamma (IFN-γ) induction in primary chicken splenocytes. As shown in FIGS. 19 and 20, Concanavalin A and ChIL-12 purified from stable transgenic plants strongly induces IFN-γ production and secretion.

FIGS. 19 and 20 depict ChIL-12$^{His}$ from transgenic lines of *N. tabacum* showing strong signature bioactivity in a dose-response fashion. Chicken splenocytes were stimulated with serial dilutions of Concanavalin A (positive control, 0-50 μg/ml) and ChIL-12$^{His}$ (0-100 ng/ml). After 48 hours of incubation at 41° C., 5% $CO_2$, the supernatants were collected and tested for ChIFN-γ levels by ELISA assay.

Example 5 Demonstrates ChIL-12-Producing Seed as a Scalable, Low-Cost Source of Chicken IL-12 Immuno-Modulator and Vaccine Adjuvant—Flax Seed as Poultry Feed Additive The inventors have selected oilseed flax (*Linum usitatissimum* L.; also called linseed) for the purpose of a commercial avian feed route of delivery for plant-derived ChIL-12. As a crop, flax has key characteristics compatible with current transgenic crop regulatory issues (Moloney & van Rooijen, 1996): 1) flax is a non-commodity specialty crop with geographically limited commercial production (>90% of U.S. crop are grown in North Dakota); 2) it is a self-pollinating crop, where out-crossing requires direct contact of parent flowers, thus limiting unintended crossing with wild relatives or displaying "weediness"; and 3) transgenic flax has successfully moved through U.S. and Canadian regulatory approval processes so regulatory agencies will not consider it "novel". Multiple flax varieties have been genetically engineered (Jain et al., 1999; ong & McHughen, 1993a; Bretagne-Sagnard & Chupeau, 1996) and the ChIL-12 transgene vectors developed in the experiments completed are directly applicable to flax transformation. Also historically, flax has been incorporated as a feed component for poultry and livestock due to its high omega-3 fatty acid content and nutritive value (Maddock et al., 2005).

*Agrobacterium*-Mediated Transformation of Flax.

Figure 22:
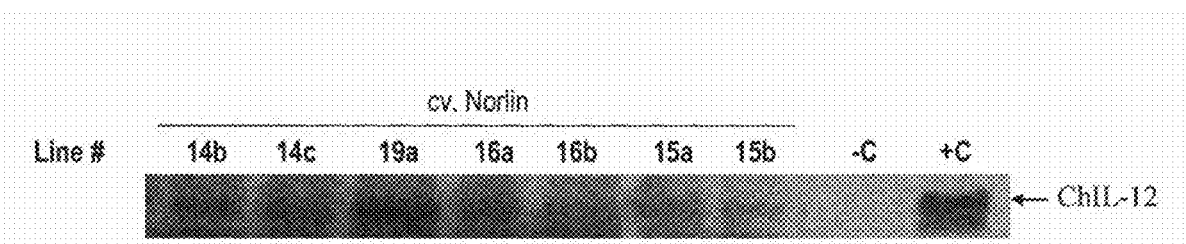
FIG. 22 is a Western immunoblot analysis of ChIL-12$^{His}$ in transgenic flax leaves.

Flax was transformed essentially following procedures outlined by Dong and McHughen 1991, 1993a,b; Beranova et al, 2008; and Yu et al, 2004. Flax seed (*Linum usitatissimum* L) of the cultivars NorLin, Normandy, and Tri-Hid were used for transformations. The 35S promoter not only drives strong transgene expression in flax seed (e.g., Jain et al., 1999), but is also active in leaves permitting identification of high-expressing lines prior to seed development, as seen in FIG. 22.

In summary, the transformation of flax was as follows: flax seeds were surface sterilized as described (Dong & McHughen, 1991) and germinated on semi-solid MS basal medium containing 3% (w/v) sucrose. Hypocotyls of 5 day old seedlings were excised and placed on "preculture" medium [MSI shoot induction medium; MS basal medium with 3% sucrose, 1.0 mg/L 6-benzylaminopurine and 0.02 mg/L α-napthalene acetic acid] and activated by an epidermal peel as described (Dong & McHughen, 1993a). Explants were immersed in *A. tumefaciens* solution (acetosyringone-induced cultures at $O.D._{600}$ of 0.4-0.6) and the explants were subjected to pulses of ultrasound delivered by a sonicator two times for 15 seconds each and co-cultivated for 2 hours at 28° C. (Beranova et al, 2007), blotted, and placed onto Whatman No. 1 filter paper layered onto MSI plates (filter paper limits *Agrobacterium* overgrowth in absence of selection). Inoculated explants were co-cultivated in MSI selection plates with 50 mg/L of kanamycin for 5-7 days prior to transfer to MSI selection plates with 500 mg/L carbenicillin and 50 mg/L kanamycin. Regenerating shoots were excised at ~1 cm (4-6 weeks), transferred to fresh selection plates, and subsequently to rooting media with 250 mg/L cefotaxime and 100 mg/L kanamycin. Plantlets that successfully initiate rooting under selective pressure (typically a strong indicator of transformation) were transferred to PlantCon containers and grown to a stage where multiple meristems could be excised and clonally propagated.

Constructs and *Agrobacterium* Strains.

His-tagged ChIL-12 construct was developed in experiments described above. This tagged transgene construct was also being introduced into *Agrobacterium* strain LBA4404 by standard freeze-thaw method and confirmed by PCR.

Selection Process of ChIL-12 Transformed Flax Lines.

Figure 21:
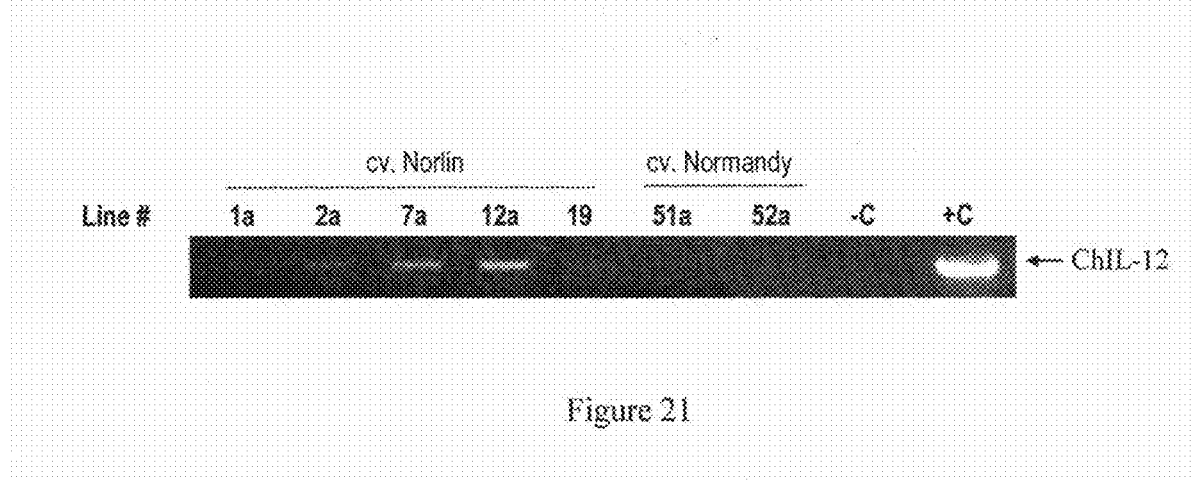
FIG. 21 is a PCR screen of ChIL-12$^{His}$ in transgenic lines of *L. usitatissimum*.

Approximately 77 independent flax transformants were developed to date, and confirmed transgenic lines were identified based on ability to root in selective media and/or by PCR and/or Western immunoblot (using either ChIL-12 primers). FIG. 21 is an example of the PCR screening of transgenic line flax leaves. The diagnostic primers used for this screen targeted the p40 region of the ChIL-12 construct. Clonally propagated leaf tissues of these initial PCR-positive flax transformants were used for protein extraction and assessment of ChIL-12 product by Western immunoblot analyses. These studies indicate relative yields of full-length (p70) product as well as the presence of any degradation products. It should be noted that an effective conformational p70 ELISA that functioned on crude extracts (i.e., had very low background with non-transgenic lines) was invaluable in rapidly screening tobacco plants for high expressers of murine IL-12. Analogous tools are currently being optimized for ChIL-12, and transgenic flax lines will be further screened by ChIL-12 ELISA for transgene expression.

FIGS. 21 and 22 demonstrate chicken IL-12 production in transgenic flax. FIG. 21 shows that genomic DNA (gDNA) from regenerant lines representing 2 cultivars were extracted using Nucleon DNA Extraction Kit (GE/Amersham Life Sciences). Five hundred nanograms of gDNA were used for each PCR reactions using primers specific for the p40-encoding region of ChIL-12$^{His}$ (ChIL-12 p40-F, ATGTCTCACCTGCTATTTGCCT (SEQ ID NO 6) and ChIL-12 p40-R, TTATCTGCAAAGCGTGGACCAC (SEQ ID NO 7). Expected amplicon size is 955 bp. FIG. 22 shows that leaves of a similar developmental stage were harvested from individual putative transgenic flax plants recovered from transformation and regeneration procedures. Leaves were processed as described for IL-12 extraction from *N. benthamiana* leaves and crude protein extracts used for ChIL-12 ELISA in order to quantify IL-12 levels (see Example 1). These lines were extracted in SDS-PAGE gel sample buffer, and the cell-free extract used for SDS-PAGE and western immunoblot using a monoclonal anti-ChIL-12 (M8) made in mouse (dilution 1:500); an anti-mouse alkaline phosphatase conjugated was used as a detection antibody. Samples are as marked; an arrow indicates the 70 kDa ChIL-12$^{His}$ product.

Lead stable transgenic flax lines expressing ChIL-12 are transferred to potting mix, subjected to vegetative clonal expansion, and taken to seed. DNA from leaf tissue of these plants are used for initial screen for transgene copy number. The inventors have developed a rapid copy-number assessment tool for screening transformed tobacco plants based on a 96-well PCR format that compares transgene levels to an endogenous gene. Briefly, leaf disks are excised using a standard office hole punch and pressed onto FTA membranes (Whatman) permitting long term storage as well as a DNA source for PCR. Small punches are excised from membrane, placed in well of 96-well microtiter plate, washed and used for PCR using primers specific for ChIL-12 (test gene) and an endogenous flax gene. PCR products are rapidly size-separated on a 96-well or a 48-well format agarose gel, scanned densitometrically, and a ratio of test-gene to endogenous gene is used to assess copy number (Dolan & Cramer, manuscript in preparation). This is used to identify homozygous production lines. They have demonstrated that this system clearly resolves transgene copy numbers in the 1-8 range and thus can be used as a first pass to identify potential homozygous lines having one or two inserts (i.e., 2 or 4 copies in the homozygous line). These analyses are also linked with ChIL-12 ELISAs to ensure that selected lines maintain high ChIL-12 expression.

The inventors anticipate that production of first generation seed requires approximately six months. Quantitative assessment of product yield is performed on first-generation seed (see above), comprise a population segregating for the ChIL-12 transgenic events. Thus, these analyses confirm lines showing strong ChIL-12 expression and demonstrate that the product is accumulated and stably stored in the seed. First generation seed (100-200 seed) is subjected to segregation analyses (kanamycin resistance) and homozygous transgenic lines are propagated for second generation seed. This seed is tested for ChIL-12 yields (ELISA and Western immunoblotting). Approximately 20 seeds of each line are germinated and ChIL-12 levels (ELISA) from developmental-matched leaf material from independent plants are quantified to confirm consistency of transgene product yield.

Propagation and Generation of Seed and Homozygous Lines.

For commercialization purposes, seed-based product yield levels are based on mature seeds of lines homozygous for the transgene. A homozygous "production line" is developed that breeds true, has a simple transgene profile (1 or 2 transgene insertions that are not tandem to minimize gene silencing potential), and expresses consistent high levels of ChIL-12 in its seed. Because the "expansion rate" of flax is relatively low (field grown plants typically yield ~70 seed, greenhouse grown plants less), the inventors will vegetatively propagate selected lines to increase seed production. Flax seeds and/or tobacco seeds (see above) containing ChIL-12 are used in feeding trials in conjunction with vaccination to demonstrate oral efficacy of ChIL-12-mediated increases in immune responses in birds.

Figure 23:
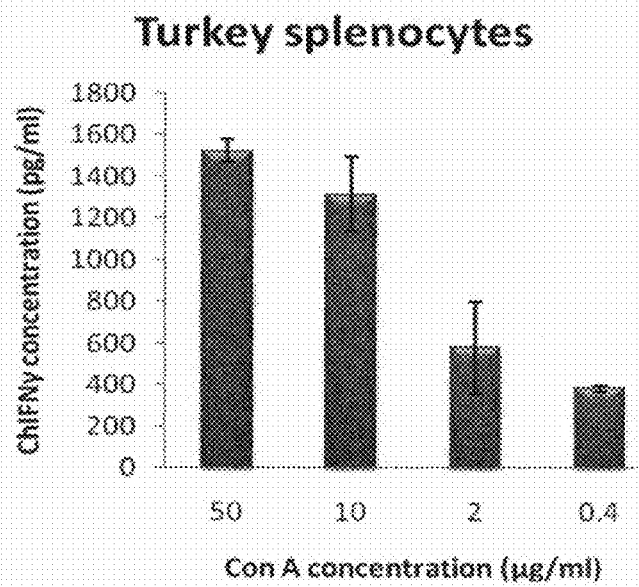
FIG. 23 depicts ChIFN-γ detection in turkey splenocyte cultures after Concanavalin A treatment (positive control)
Figure 24:
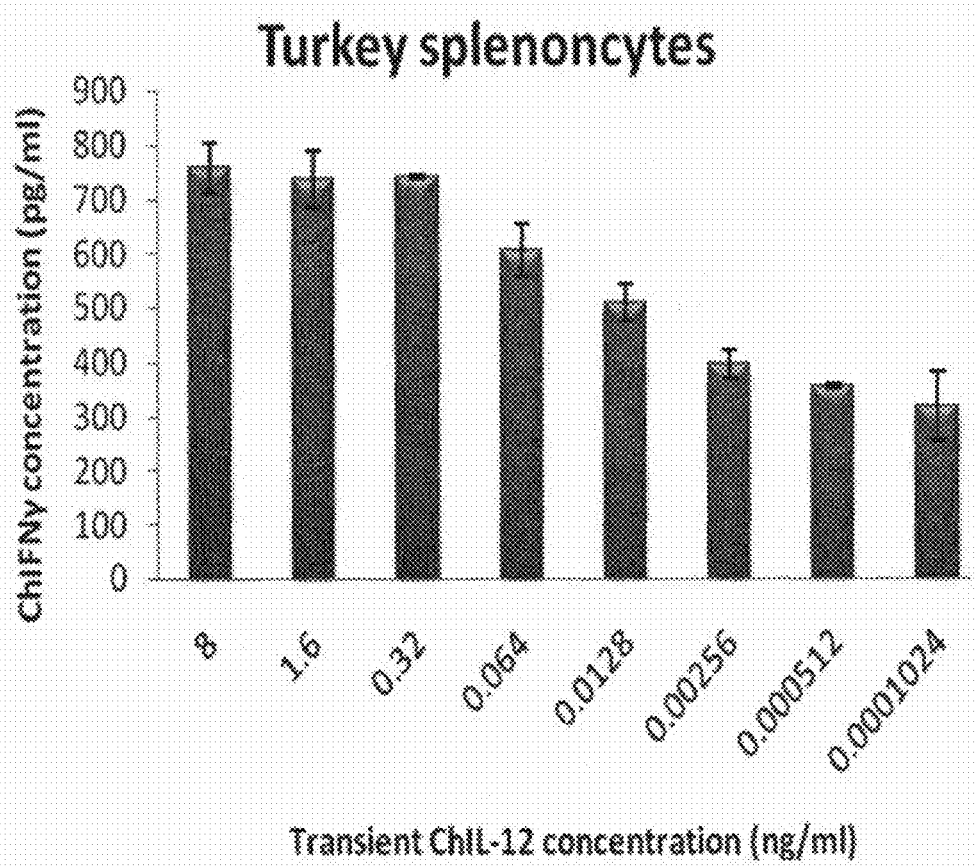
FIG. 24 depicts ChIFN-γ detection in turkey splenocyte cultures after plant-derived ChIL-12$^{His}$ treatment showing strong dose-dependent IL-12 bioactivity on turkey splenocytes.

Example 6 Demonstrates that Cross-Species Bioactivity of ChIL-12 Broadens Product Applications and Markets Chickens represent the species having the greatest population of birds among domestic poultry. However, species such as turkeys have significantly higher value per bird and have increased time to maturity, thereby, enhancing producer interest in disease prevention strategies for commercial flocks and breeder stocks. Additionally, in a major national response to a significant HPAI (e.g., $H_5N_1$ with human pandemic implications) outbreak among wild fowl in the U.S., there may be substantial interest in utilizing a non-viable-seed-based strategy for vaccinating wild birds to reduce the disease sink. For example, flax seed containing both chicken IL-12 and avian flu protective antigens, such as M2e and H5-HA, could be irradiated or milled to eliminate seed viability (addressing GM release issues) and used directly for field distribution in major feeding regions of the U.S. flyways or over-winter ground (e.g., Arkansas) or incorporated into feed pellets for water release for dabbling species. Thus, there is significant interest in determining whether plant-produced ChIL-12 functions as an immune activator in other domesticated and wild avian species, specifically turkeys, ducks, and geese. Sequence comparisons between published chicken IL-12p40 sequences and turkey (*Meleagris gallopavo*) IL-12p40 (the only avian IL-12 sequences in the databases) revealed 95% sequence identity (98% similarity) at the amino acid level. This high degree of sequence relatedness suggests that ChIL-12 has the conformational similarity to interact with IL-12 receptors on splenocytes from turkey and other avian species. To test for ChIL-12 bioactivity on other avian species, the inventors utilized the in vitro splenic interferon-gamma (IFN-γ) induction assay described for chicken splenocytes. FIGS. 23 and 24 depict plant-derived ChIL-12$^{His}$ showing strong signature bioactivity on turkey splenocytes. Primary turkey splenocytes cultures were induced with Concanavalin A (positive control, 0-50 μg/ml) and ChIL-12$^{His}$ (0-10 ng/ml). Serial dilutions of ChIL-12 were added and cells were incubated for 48 hours at 41° C., 5% $CO_2$. After the incubation period, the supernatants were collected for assessment of IFN-γ induction by using ChIFNγ ELISA kit (Invitrogen).

FIGS. 23 and 24 depict plant-derived ChIL-12$^{His}$ showing strong signature bioactivity on turkey splenocytes. Turkey splenocytes were stimulated with serial dilutions of Concanavalin A (positive control, 0-50 μg/ml) and ChIL-12$^{His}$ (0-10 ng/ml). After 48 h of incubation at 41° C., 5% $CO_2$, supernatants were collected and tested for ChIFN-γ levels by ELISA assay.

REFERENCES

Albu, D. I., A. Jones-Trower, A. M. Woron, K. Stellrecht, C. C. Broder, and D. W. Metzger. 2003. Intranasal vaccination using interleukin-12 and cholera toxin subunit B as adjuvants to enhance mucosal and systemic immunity to human immunodeficiency virus type 1 glycoproteins. *J. Virol.* 77:5589-5597.

Arulanandam, B. P., M. O'Toole, and D. W. Metzger. 1999. Intranasal interleukin-12 is a powerful adjuvant for protective mucosal immunity. *J. Infect. Dis.* 180:940-949.

Arulanandam, B. P., J. M. Lynch, D. E. Briles, S. Hollingshead, and D. W. Metzger. 2001a. Intranasal vaccination with pneumococcal surface protein A and interleukin-12 augments antibody-mediated opsonization and protective immunity against *Streptococcus pneumoniae* infection. *Infect. Immun.* 69:6718-6724.

Bowen, O. T., G. F. Erf, N. B. Anthony, and R. F. Wideman. 2006a. Pulmonary hypertension triggered by lipopolysaccharide in ascites-susceptible and -resistant broilers is not amplified by aminoguanidine, a specific inhibitor of inducible nitric oxide synthase. *Poult. Sci.* 85:528-536.

Bowen, O. T., R. F. Wideman, N. B. Anthony, and G. F. Erf. 2006b. Variation in the pulmonary hypertensive responsiveness of broilers to lipopolysaccharide and innate variation in nitric oxide production by mononuclear cells. *Poult. Sci.* 85:1349-1363.

Boyaka, P. N., M. Marinaro, R. J. Jackson, S. Menon, H. Kiyono, E. Jirillo, and J. R. McGhee. 1999. IL-12 is an effective adjuvant for induction of mucosal immunity. J. Immunol. 162:122-128.

Bretagne-Sagnard, B., and Y. Chupeau. 1996. Selection of transgenic flax plants is facilitated by spectinomycin. *Transgen. Res.* 5:131-137.

Dong, J. and A. McHughen. 1993a. An improved procedure for production of transgenic flax plants using *Agrobacterium tumefaciens*. *Plant Science.* 88:61-71.

Dong, J. and A. McHughen. 1993b. Transgenic flax plants from *Agrobacterium* mediated transformation: incidence of chimeric regenerants and inheritance of transgenic plants. Plant Science. 91:139-148.

Gutierrez-Ortega, A., F. Avila-Moreno, L. J. Saucedo-Arias, C. Sanchez-Tones, and M. A. Gomez-Lim. 2004. Expression of a single-chain human interleukin-12 gene in transgenic tobacco plants and functional studies. *Biotechnol. Bioeng.* 85:734-740.

Gutierrez-Ortega A, Sandoval-Montes C, Olivera-Flores T J, Santos-Argumedo L, and Gomez-Lim M A. Expression of functional interleukin-12 from mouse in transgenic tomato plants. *Transgenic Res.* 2005; 14:877-885.

Huber, V. C., J. M. Lynch, D. J. Bucher, J. Le, and D. W. Metzger. 2001. Fc receptor-mediated phagocytosis makes a significant contribution to clearance of influenza virus infections. J. Immunology. 166:7381-7388.

Kwon, T. H., J. E. Seo, J. Kim, J. H. Lee, Y. S. Jang, and M. S. Yang. 2003. Expression and secretion of the heterodimeric protein interleukin-12 in plant cell suspension culture. *Biotechnol. Bioeng.* 81:870-875.

Lambrecht, B., M. Gonze, D. Morales, G. Meulemans, T. P. van den Berg. 1999. Comparison of biological activities of natural and recombinant chicken interferon-gamma. *Vet. Immunol. Immunopathol.* 70:257-267.

Lyn, T. F. 2008. Experts urge stockpiling of flu vaccine additives, Reuters News Service, Jan. 23, 2008

Lynch, J. M., D. E. Briles, and D. W. Metzger. 2003. Increased protection against pneumococcal disease by mucosal administration of conjugate vaccine plus interleukin-12. *Infect. Immun.* 71:4780-4788.

Maddock, T. D., C. L. Anderson, and G. P. Lardy. 2005. Using flax in livestock diets. NDSU Extension Service online publication. http://www.ag.ndsu.edu/pubs/ansci/beef/as1283.pdf Masurel N., P. Ophof, and P. de Jong. 1981. Antibody response to immunization with influenza A/USSR/77 ($H_1N_1$) virus in young individuals primed or unprimed for A/New Jersey/76 (H1N1) virus. *J Hyg* 87:201-209.

McLain L., D. J. Morgan, and N. J. Dimmock. 1992. Protection of mice from lethal influenza by defective interfering virus: T cell responses. *J Gen Virol.* 73:375-81.

Medina-Bolivar, F., R. Wright, V. Funk, D. Sentz, L. Barroso, T. D. Wilkins, W. Petri, Jr., and C. L. Cramer. 2003. A non-toxic lectin for antigen delivery of plant-based mucosal vaccines. *Vaccine* 21:997-1005.

Medina-Bolivar, F. and C. Cramer. 2004. Production of recombinant proteins by hairy roots cultured in plastic sleeve bioreactors. *Methods Mol. Biol.* 267:351-363.

Medrano, G., M. J. Reidy, J. Liu, J. Ayala, M. C. Dolan, and C. L. Cramer. Rapid system for evaluating bioproduction capacity of complex pharmaceutical proteins in plants. In Methods in Biotechnology "Recombinant Pharmaceutical Proteins from Plants", Humana Press, USA, pp. 51-68.

Moloney, M. M., and G. J. H. van Rooijen. 1996. Seed-derived recombinany proteins using oleosin partitioning technology. *International News of Fats, Oils and Related Materials* (INFORM). 7:107-113.

Orson, F. M., B. M. Kinsey, C. L. Densmore, T. Nguyen, Y. Wu, I. N. Mbawuike, and P. R. Wyde. 2006. Protection against influenza infection by cytokine-enhanced aerosol genetic immunization. *J. Gene Med.* 8:488-497.

Pantin-Jackwood M. J., D. L. Suarez, E. Spackman, and D. E. Swayne. 2007. Age at infection affects the pathogenicity of Asian highly pathogenic avian influenza $H_5N_1$ viruses in ducks. *Virus Res.* 130:151-61.

Sacco, S., H. Heremans, B. Echtenacher, W. A. Buurman, Z. Amraoui, M. Goldman, and P. Ghezzi. 1997. Protective effect of a single interleukin-12 (IL-12) predose against the toxicity of subsequent chronic IL-12 in mice: role of cytokines and glucocorticoids. *Blood.* 90:4473-4479.

Salem, M. L., W. E. Gillanders, A. N. Kadima, S. El-Naggar, M. P. Rubinstein, M. Demcheva, J. N. Vournakis, and D. J. Cole. 2006. Novel non-viral delivery approaches for IL-12 protein and gene systems: curbing toxicity and enhancing adjuvant activity. *J. Interferon Cytokine Res.* 26(9): 593-608.

Vancanneyt, G., R. Schmidt, A. O'Connor-Sanchez, I. Willmitzer, and M. Rocha-Sosa. 1990. Construction of intron-containing marker gene: splicing of the intron in transgenic plants and its use in monitoring early events in *Agrobacterium*-mediated plant transformation. *Mol. Gen. Genet.* 220:245-250.

---

We claim:

1. A method for producing an avian interleukin-12 protein comprising a p35 alpha chain and a p40 beta chain, wherein the p40 beta chain comprises an amino acid sequence having at least about 95% identity or about 98% similarity at the amino acid level to that of chicken IL-12 p40, or a fragment thereof (collectively "avIL-12"), wherein said avIL-12 produces IL-12-mediated immuno-modulating activity in chicken or turkey or immune cells thereof, the method comprising expressing said protein or fragment thereof in a plant cell.

2. The method of claim 1, wherein said method for producing an avIL-12 protein comprises transforming a plant cell with a nucleic acid sequence that encodes an avIL-12 protein and cultivating a transformed plant host under conditions to express said avIL-12 protein.

3. The method of claim 2, wherein said expressed avIL-12 protein is recovered from said plant cell.

4. The method of claim 1 wherein said avIL-12 protein is transiently expressed in said plant cell.

5. The method of claim 1 wherein said avIL-12 protein is stably expressed in said plant cell.

6. The method of claim 1 wherein said avIL-12 protein is produced by expressing in said plant cell at least one p35 alpha chain and at least one p40 beta chain such that said at least one p35 alpha chain and said at least one p40 beta chain form said protein in said plant cell.

7. The method of claim 1, wherein said avIL-12 protein is produced at levels of at least about 0.1% total soluble protein.

8. A plant expressing an avian interleukin-12 protein comprising a p35 alpha chain and a p40 beta chain, wherein the p40 beta chain comprises an amino acid sequence having at least about 95% identity or about 98% similarity at the amino acid level to that of chicken IL-12 p40, or a fragment thereof (collectively "avIL-12"), wherein said avIL-12 produces IL-12-mediated immuno-modulating activity in chicken or turkey or immune cells thereof.

9. The plant of claim 8 wherein said avIL-12 protein is expressed in said plant cell at a level of at least 0.1% of total soluble protein.

10. A cell of a plant of claim 8.

11. A component of a plant of claim 8, selected from the group consisting of seed, leaf, root, stem and tissue of said plant.

* * * * *

SEQUENCE LISTING

```
<160> NUMBER OF SEQ ID NOS: 7

<210> SEQ ID NO 1
<211> LENGTH: 1521
<212> TYPE: DNA
<213> ORGANISM: Artificial Sequence
<220> FEATURE:
<223> OTHER INFORMATION: Single chain form of chIL-12 using native DNA
      sequence

<400> SEQUENCE: 1
atgtctcacc tgctatttgc cttactttca ttactttcct ttgctgccct tctggaagca      60
cagtggaaac ttagagagaa tgtgtatgtc atagaatctg agtggaacga tgagacacca     120
gctaaaaaag tgaagctcac ctgtgacaca tctgatgaag cactgccagt ttactggaaa     180
aagggaacag aactgaaagg aactggaaag actctgacca ccgaagtgaa ggagttccca     240
gatgctggca actacacctg cctgtctgct aagacccacg agattatcag ctacagtttc     300
tttctcataa ctaaagtaga ctccaatggg caaatgatac ggtcaattct gaaaagctac     360
aaagagccaa gcaagacgtt cttaaaatgt gaggcaaaga actactctgg aattttcaca     420
tgttcatgga tgacagaaaa tgagagtcca agtgtgaagt tcacaattag gagcctaaaa     480
ggctctcaag gagatgtaac ctgcagcagc cctgtggctc gcactgacaa atctgtgact     540
gaatacactg cccagtgcca gaaggaaaac tactgtccat ttgccgaaga gcaccagccg     600
actgagatgt tcctggaggt cattgatgag gtggaatatg agaactacac tagtagcttc     660
ttcatcagag atatcattaa gccagaccca cctcaatgtc agtatgcaag cacaaatgga     720
actgtgacct ggacatatcc caagacctgg agcacaccga gtcctactt ccctttgact     780
```

-continued

| | |
|---|---|
| ttcagggtca aagttgaaag cacaaagaag tacaaaagca aggtttatga tgctgatgag | 840 |
| cagtctattc agattccaaa gactgggcca aagacaaga tctctgtgca ggccagggat | 900 |
| cgctattaca actcatcctg gagtgagtgg tccacgcttt gcagaggtgg cggtggctcg | 960 |
| ggcggtggtg ggtcgggtgg cggcggatcc ctgccacctc ctgcccacaa cctggccaag | 1020 |
| ggactcaact gctccagggc gctgctggcc gctgcaaacg aggcactcct gaaggtgcag | 1080 |
| aagcagagga cgctggggtt tgagtgcacc cttgaagagg tcgatcttga agacgtcacc | 1140 |
| aacagtcaga gcaacacgat caagtcctgc acgtctcaag atccggggcc tggaaactgc | 1200 |
| cccgtactgg aaagttctac tttagatatg agcaaatgcc tgcaggggat ctacgaagac | 1260 |
| ctgaaaacct acaaggcaga gctggggaac ctcaaggatc tgagggtgct gacatccatt | 1320 |
| gatgacatga tgcaagccct gcagcccgc agcccagcca tgcgcagcc tcgcccagc | 1380 |
| accacccttg gctccttcca gggccgcatg cggctctgcg gggtcctgca cgccttctgc | 1440 |
| ctgcgcgcag tcaccatcgg caggatgctg ggctacctga gtgccctcac tgcagagatg | 1500 |
| catcaccatc accatcatta a | 1521 |

<210> SEQ ID NO 2
<211> LENGTH: 1521
<212> TYPE: DNA
<213> ORGANISM: Artificial Sequence
<220> FEATURE:
<223> OTHER INFORMATION: Single chain form of chIL-12 using codon-optimized DNA sequence

<400> SEQUENCE: 2

| | |
|---|---|
| atgtcccatt tgttattcgc tttactatct ctactatctt ttgcagcctt actagaagcc | 60 |
| caatggaagc taagagaaaa cgtgtatgtt attgaatccg aatggaatga cgaaactcct | 120 |
| gctaaaaaag tgaaattaac ctgcgatacc tcagatgaag ccctacccgt ttactggaaa | 180 |
| aaaggcacag aactaaaagg aacaggaaaa acacttacaa ccgaagttaa agaattccca | 240 |
| gacgccggca actacacatg cttatcagct aagacacacg ataaatttc ttattcattc | 300 |
| tttctaatta ctaaggtaga ctcaaacggc caaatgatac gatcaatact aaagtcctac | 360 |
| aaagaacctt ctaaaacatt cctaaaatgc gaggcaaaaa actactcagg aatttttaca | 420 |
| tgctcatgga tgaccgaaaa cgaaagccct agcgttaagt ttactataag aagtctaaag | 480 |
| ggatctcaag gagacgttac atgtagttcc ccagttgcaa gaactgacaa atctgttaca | 540 |
| gaatacactg ctcaatgcca aaagaaaat tactgcccct cgctgaaga acatcaacca | 600 |
| actgaaatgt ttctcgaagt tatcgacgaa gttgaatatg aaaactatac ttcatctttt | 660 |
| ttcatccgtg atatcattaa acctgaccca cctcaatgtc aatatgctag taccaatgga | 720 |
| acagtaacat ggacttaccc taaaacttgg tctactccta gagctactt tccactaacc | 780 |
| ttccgtgtta agttgaatc taccaagaag tacaagtcaa agtatacga cgcagacgaa | 840 |
| caatctattc aaatcccaaa gacaggccca aaggacaaga tatctgtgca agcaagagac | 900 |
| cgatactata tagctcatg gtcagaatgg tcaacattat gtaggggtgg tggcggatca | 960 |
| ggaggaggtg gttctggagg aggaggatcc ctgcccccac cagcacacaa tcttgcaaaa | 1020 |
| ggtcttaatt gttccagagc ccttttagct gctgcaaatg aagctctcct taaagttcaa | 1080 |
| aaacaaagaa ctctcggttt tgaatgcacc ttagaagagg tagatttgga agacgttact | 1140 |
| aattcacaat ccaacacaat taagtcatgt actagtcagg accccggacc aggaaattgc | 1200 |
| cccgttttag aatcctcaac tcttgatatg tcaagtgcc ttcagggaat ctatgaagat | 1260 |
| ctgaaaactt acaaagctga acttggaaac cttaaagatc ttagagtttt aacctctatc | 1320 |

```
gacgatatga tgcaagcact acaacccgt tcaccagcta tgccacaacc ttccccttca    1380
accacactag gttctttcca aggtagaatg agattatgcg gagtcctaca tgctttctgt    1440
ttacgtgctg ttaccattgg tagaatgctt ggataccttt ctgcacttac tgctgaaatg    1500
caccaccacc atcatcatta a                                              1521
```

<210> SEQ ID NO 3
<211> LENGTH: 506
<212> TYPE: PRT
<213> ORGANISM: Gallus gallus

<400> SEQUENCE: 3

```
Met Ser His Leu Leu Phe Ala Leu Leu Ser Leu Ser Phe Ala Ala
1               5                  10                  15

Leu Leu Glu Ala Gln Trp Lys Leu Arg Glu Asn Val Tyr Val Ile Glu
            20                  25                  30

Ser Glu Trp Asn Asp Glu Thr Pro Ala Lys Lys Val Lys Leu Thr Cys
        35                  40                  45

Asp Thr Ser Asp Glu Ala Leu Pro Val Tyr Trp Lys Lys Gly Thr Glu
    50                  55                  60

Leu Lys Gly Thr Gly Lys Thr Leu Thr Thr Glu Val Lys Glu Phe Pro
65                  70                  75                  80

Asp Ala Gly Asn Tyr Thr Cys Leu Ser Ala Lys Thr His Glu Ile Ile
                85                  90                  95

Ser Tyr Ser Phe Phe Leu Ile Thr Lys Val Asp Ser Asn Gly Gln Met
            100                 105                 110

Ile Arg Ser Ile Leu Lys Ser Tyr Lys Glu Pro Ser Lys Thr Phe Leu
        115                 120                 125

Lys Cys Glu Ala Lys Asn Tyr Ser Gly Ile Phe Thr Cys Ser Trp Met
    130                 135                 140

Thr Glu Asn Glu Ser Pro Ser Val Lys Phe Thr Ile Arg Ser Leu Lys
145                 150                 155                 160

Gly Ser Gln Gly Asp Val Thr Cys Ser Ser Pro Val Ala Arg Thr Asp
                165                 170                 175

Lys Ser Val Thr Glu Tyr Thr Ala Gln Cys Gln Lys Glu Asn Tyr Cys
            180                 185                 190

Pro Phe Ala Glu Glu His Gln Pro Thr Glu Met Phe Leu Glu Val Ile
        195                 200                 205

Asp Glu Val Glu Tyr Glu Asn Tyr Thr Ser Ser Phe Phe Ile Arg Asp
    210                 215                 220

Ile Ile Lys Pro Asp Pro Pro Gln Cys Gln Tyr Ala Ser Thr Asn Gly
225                 230                 235                 240

Thr Val Thr Trp Thr Tyr Pro Lys Thr Trp Ser Thr Pro Lys Ser Tyr
                245                 250                 255

Phe Pro Leu Thr Phe Arg Val Lys Val Glu Ser Thr Lys Lys Tyr Lys
            260                 265                 270

Ser Lys Val Tyr Asp Ala Asp Glu Gln Ser Ile Gln Ile Pro Lys Thr
        275                 280                 285

Gly Pro Lys Asp Lys Ile Ser Val Gln Ala Arg Asp Arg Tyr Tyr Asn
    290                 295                 300

Ser Ser Trp Ser Glu Trp Ser Thr Leu Cys Arg Gly Gly Gly Ser
305                 310                 315                 320

Gly Gly Gly Gly Ser Gly Gly Gly Ser Leu Pro Pro Ala His
                325                 330                 335
```

-continued

```
Asn Leu Ala Lys Gly Leu Asn Cys Arg Ser Arg Ala Leu Leu Ala Ala
                340                 345                 350

Ala Asn Glu Ala Leu Leu Lys Val Gln Lys Gln Arg Thr Gly Phe Glu
            355                 360                 365

Cys Thr Leu Glu Glu Val Asp Leu Glu Asp Val Thr Asn Ser Gln Ser
    370                 375                 380

Asn Thr Ile Lys Ser Cys Thr Ser Gln Asp Pro Gly Pro Asn Cys
385                 390                 395                 400

Pro Val Leu Glu Ser Ser Thr Leu Asp Met Ser Lys Cys Leu Gln Gly
                405                 410                 415

Ile Tyr Glu Asp Leu Lys Thr Tyr Lys Ala Glu Leu Gly Asn Leu Lys
            420                 425                 430

Asp Leu Arg Val Leu Thr Ser Ile Asp Asp Met Met Gln Ala Leu Gln
            435                 440                 445

Pro Arg Ser Pro Ala Met Pro Gln Pro Ser Pro Ser Thr Thr Leu Gly
        450                 455                 460

Ser Phe Gln Gly Arg Met Arg Leu Cys Gly Val Leu His Ala Phe Cys
465                 470                 475                 480

Leu Arg Ala Val Thr Ile Gly Arg Met Leu Gly Tyr Leu Ser Ala Leu
                485                 490                 495

Thr Ala Glu Met His His His His His His
            500                 505

<210> SEQ ID NO 4
<211> LENGTH: 42
<212> TYPE: DNA
<213> ORGANISM: Artificial Sequence
<220> FEATURE:
<223> OTHER INFORMATION: Primer for Kpn-chIL-12-F

<400> SEQUENCE: 4
gcggtaccat gtctcacctg ctatttgcct tactttcatt ac                         42

<210> SEQ ID NO 5
<211> LENGTH: 42
<212> TYPE: DNA
<213> ORGANISM: Artificial Sequence
<220> FEATURE:
<223> OTHER INFORMATION: Primer for Sac-Stop-chIL-12-R

<400> SEQUENCE: 5
cggagctctt acatctctgc agtgagggca ctcaggtagc cc                         42

<210> SEQ ID NO 6
<211> LENGTH: 22
<212> TYPE: DNA
<213> ORGANISM: Artificial Sequence
<220> FEATURE:
<223> OTHER INFORMATION: Primer for chIL-12 p40-F

<400> SEQUENCE: 6
atgtctcacc tgctatttgc ct                                               22

<210> SEQ ID NO 7
<211> LENGTH: 22
<212> TYPE: DNA
<213> ORGANISM: Artificial Sequence
<220> FEATURE:
<223> OTHER INFORMATION: Primer for chIL-12 p40-R
```

```
<400> SEQUENCE: 7
ttatctgcaa agcgtggacc ac                                                      22
```